US012714779B2

(12) United States Patent
Arcand et al.

(10) Patent No.: US 12,714,779 B2
(45) **Date of Patent: *Aug. 25, 2026**

(54) SYRINGE-BASED MICROBUBBLE GENERATOR WITH AN AERATOR

(71) Applicant: Agitated Solutions Inc., Oakdale, MN (US)

(72) Inventors: Benjamin Arcand, Minneapolis, MN (US); Carl Lance Boling, San Jose, CA (US)

(73) Assignee: Agitated Solutions Inc., St. Paul, MN (US)

(*) Notice: Subject to any disclaimer, the term of this patent is extended or adjusted under 35 U.S.C. 154(b) by 1095 days.

This patent is subject to a terminal disclaimer.

(21) Appl. No.: 17/584,826

(22) Filed: Jan. 26, 2022

(65) Prior Publication Data

US 2022/0233762 A1 Jul. 28, 2022

Related U.S. Application Data

(63) Continuation-in-part of application No. 17/566,079, filed on Dec. 30, 2021, now Pat. No. 11,400,207, which is a continuation-in-part of application No. 17/542,386, filed on Dec. 4, 2021, now Pat. No. 11,951,277, which is a continuation of application No. 17/158,396, filed on Jan. 26, 2021, now Pat. No. 11,191,888.

(51) Int. Cl.

| | |
|---|---|
| ***A61M 5/00*** | (2006.01) |
| ***A61K 49/22*** | (2006.01) |
| ***A61M 5/14*** | (2006.01) |
| ***A61M 5/145*** | (2006.01) |

(52) U.S. Cl.

CPC .......... *A61M 5/007* (2013.01); *A61K 49/223* (2013.01); *A61M 5/00* (2013.01); *A61M 5/1452* (2013.01); *A61M 5/1408* (2013.01)

(58) Field of Classification Search

CPC ...... A61M 5/007; A61M 5/00; A61M 5/1452; A61M 5/1408; A61K 49/223

See application file for complete search history.

(56) References Cited

U.S. PATENT DOCUMENTS

| | | | | |
|---|---|---|---|---|
| 5,211,627 A * | 5/1993 | William | A61M 25/003 | 604/82 |
| 5,380,411 A * | 1/1995 | Schlief | A61N 7/00 | 601/4 |

(Continued)

*Primary Examiner* — Lauren P Farrar
*Assistant Examiner* — Leah J Swanson
(74) *Attorney, Agent, or Firm* — Matthew J. Smyth

(57) ABSTRACT

A device includes a syringe having a barrel and a syringe tip; an aerator having (i) a generally cylindrical exterior body; (ii) an inlet end; (iii) an outlet end; (iv) a tapered outlet port at its outlet end; and (v) an interior cavity comprising (A) an input port section, (B) a converging section, (C) a throat section, (D) a diverging section, (E) an outlet section, (F) a first vent that fluidly couples at least one of the throat section or the diverging section to an area outside and adjacent to the exterior body, and (G) a second vent that fluidly couples the outlet section to the area; and a housing that (x) circumferentially surrounds an end of the barrel and the aerator, (z) has an interior surface, (aa) forms a circumferential gas pocket between the interior surface and the exterior body, and (bb) has a housing discharge tip.

10 Claims, 21 Drawing Sheets

(56) References Cited

U.S. PATENT DOCUMENTS 5,585,112 A * 12/1996 Unger .................. A61K 9/1278
264/4.1
11,400,207 B1 * 8/2022 Arcand ............... B01F 35/7174
2014/0155745 A1 * 6/2014 Duncan ............... A61M 31/005
600/435
2015/0133779 A1 * 5/2015 Yurek .................... A61B 8/481
600/435

* cited by examiner 353
339
333
347
341
315
300
327
330
302
306
303
309

356
339
347
303
309

356
333
347
346
341
300
315
327
330
302
303
309

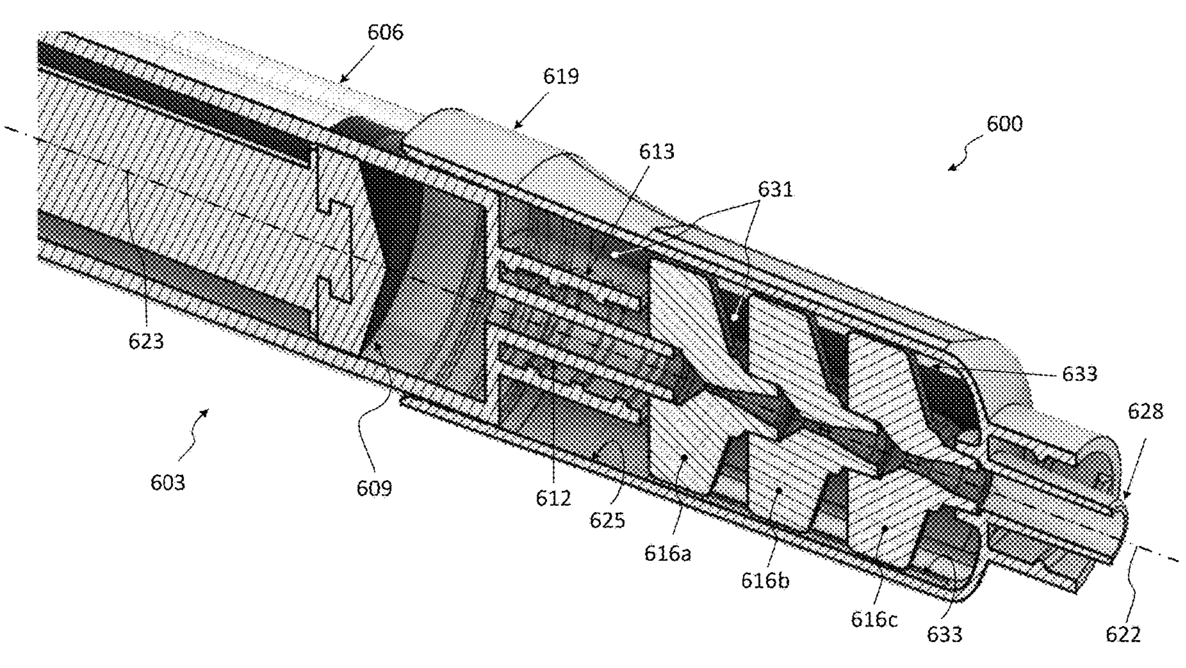
FIG. 6A
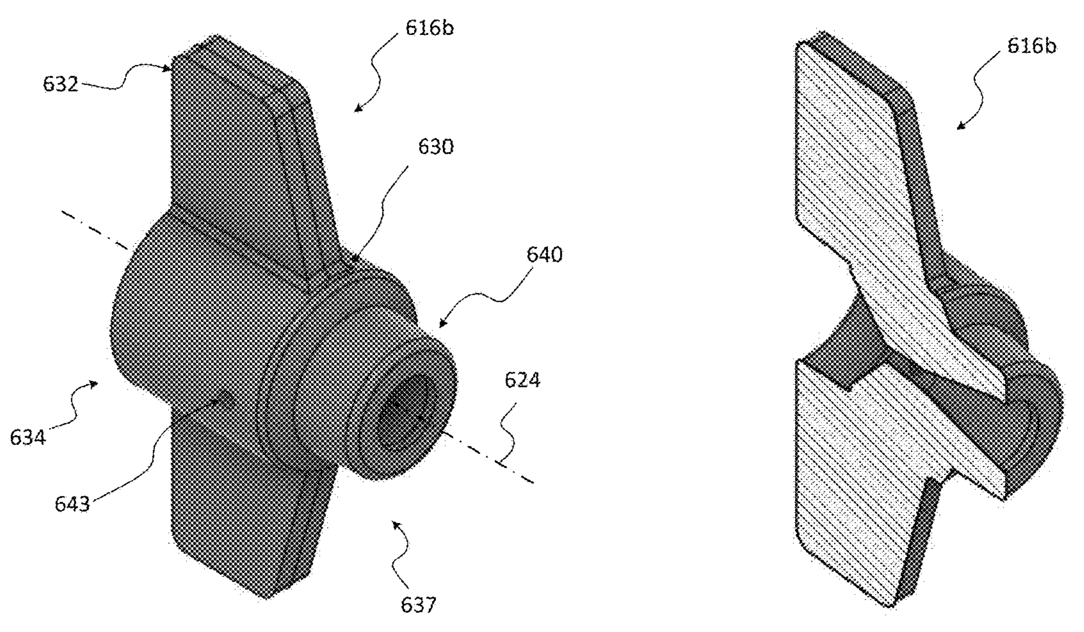
FIG. 6B
FIG. 6C

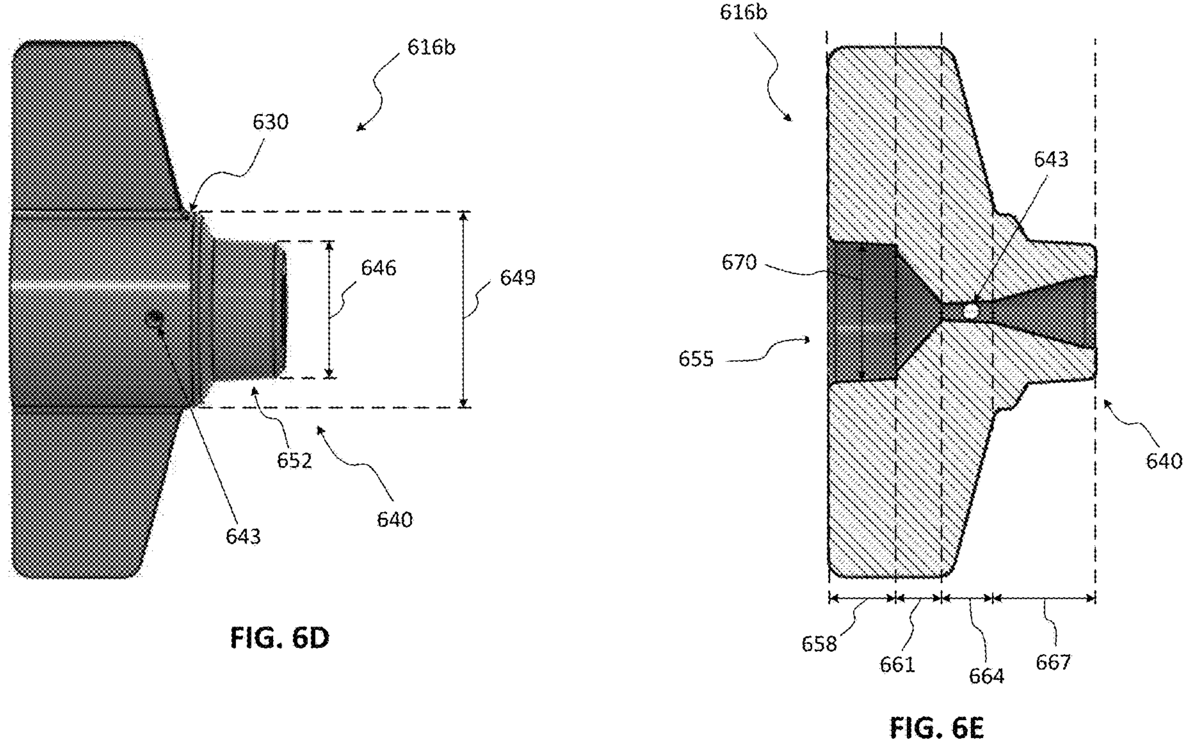
FIG. 6D
FIG. 6E
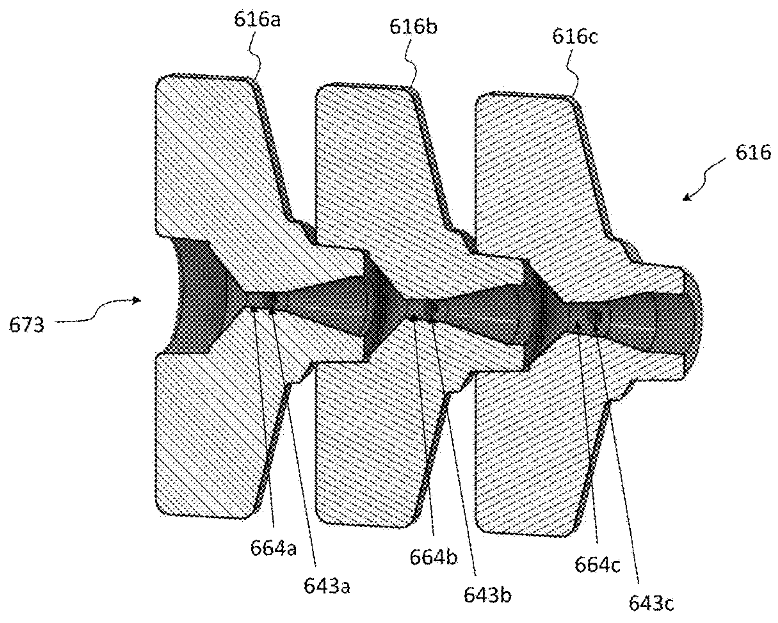
FIG. 6F

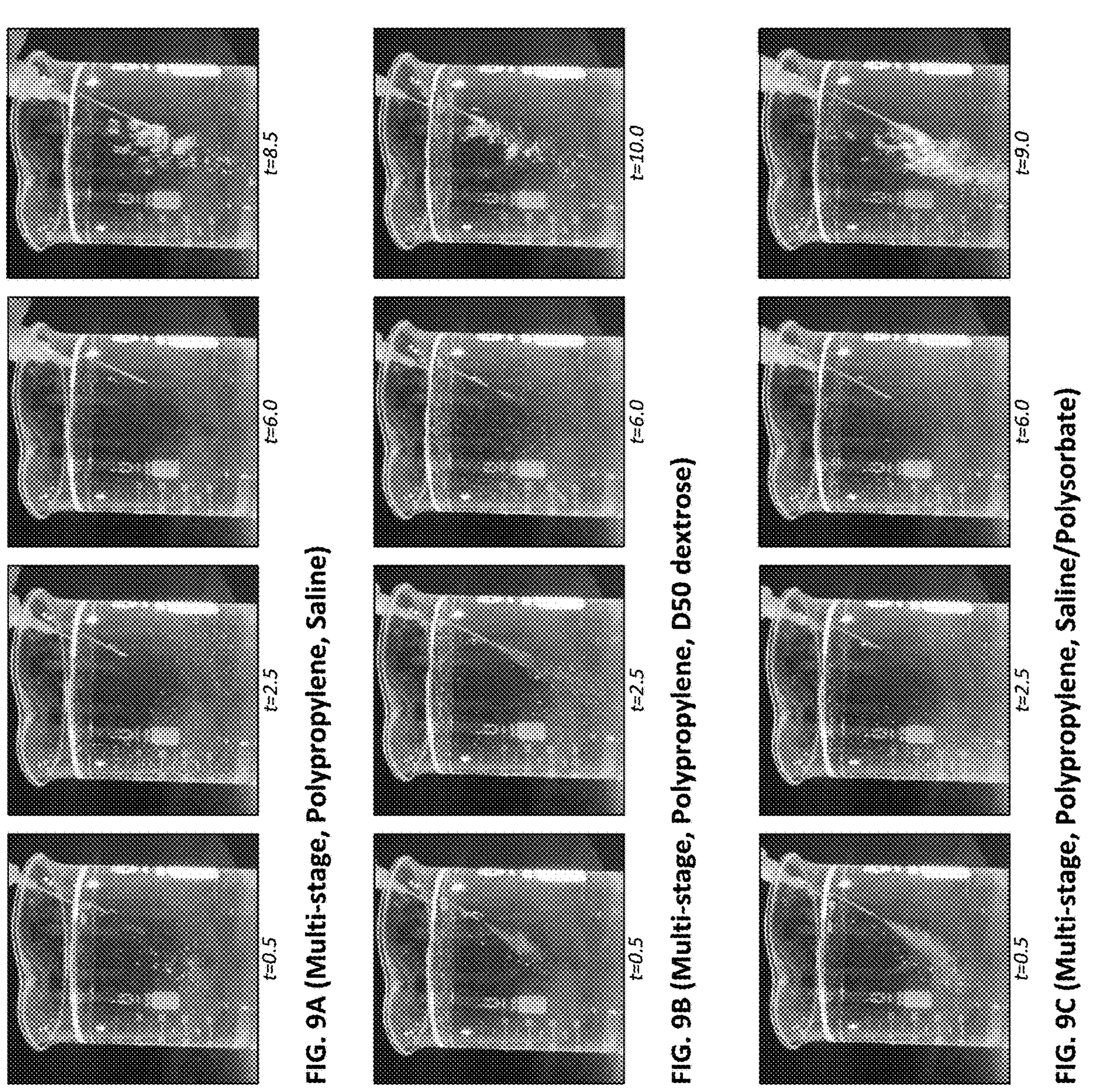
FIG. 9A (Multi-stage, Polypropylene, Saline)
FIG. 9B (Multi-stage, Polypropylene, D50 dextrose)
FIG. 9C (Multi-stage, Polypropylene, Saline/Polysorbate)

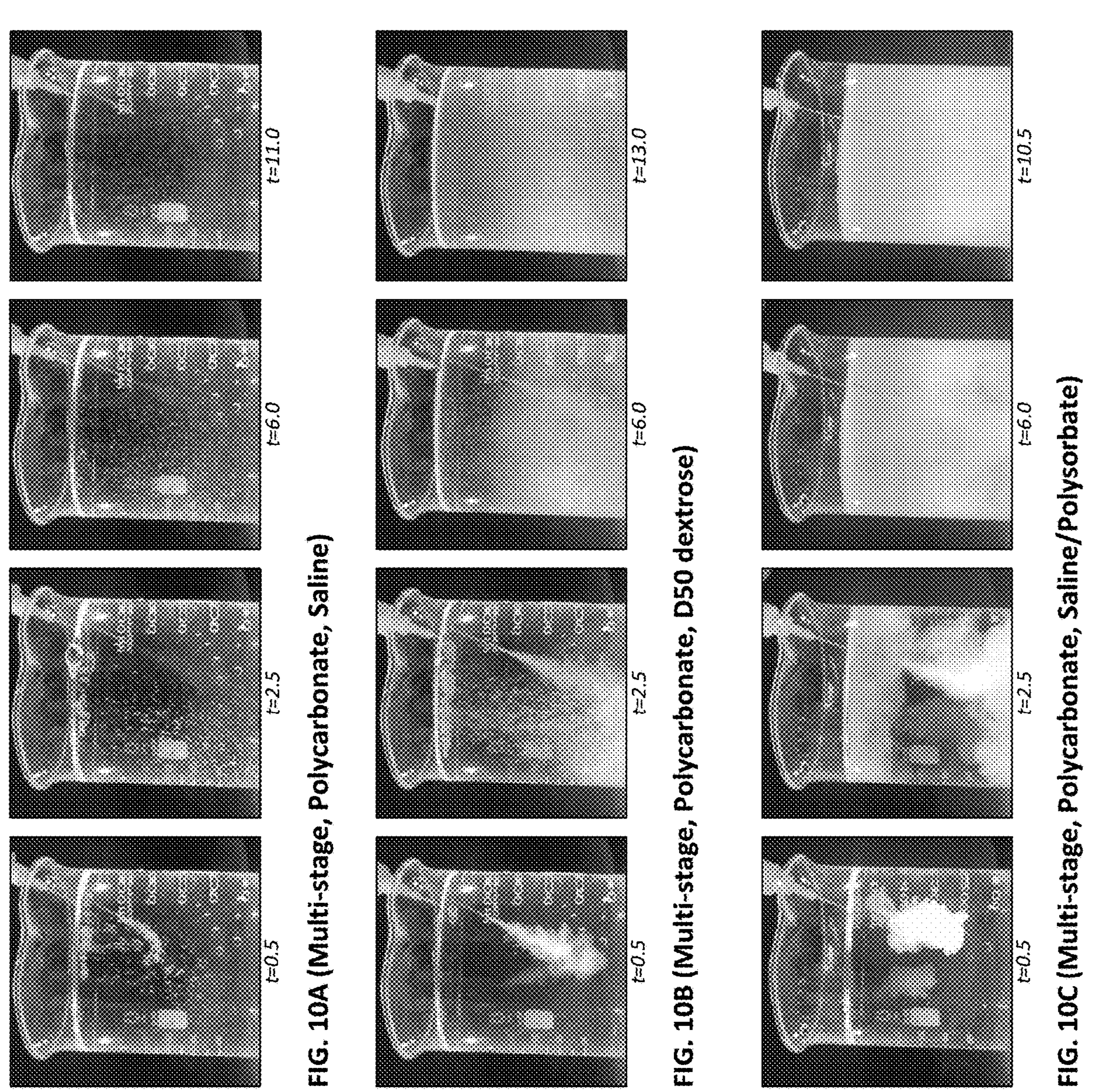
FIG. 10A (Multi-stage, Polycarbonate, Saline)
FIG. 10B (Multi-stage, Polycarbonate, D50 dextrose)
FIG. 10C (Multi-stage, Polycarbonate, Saline/Polysorbate)

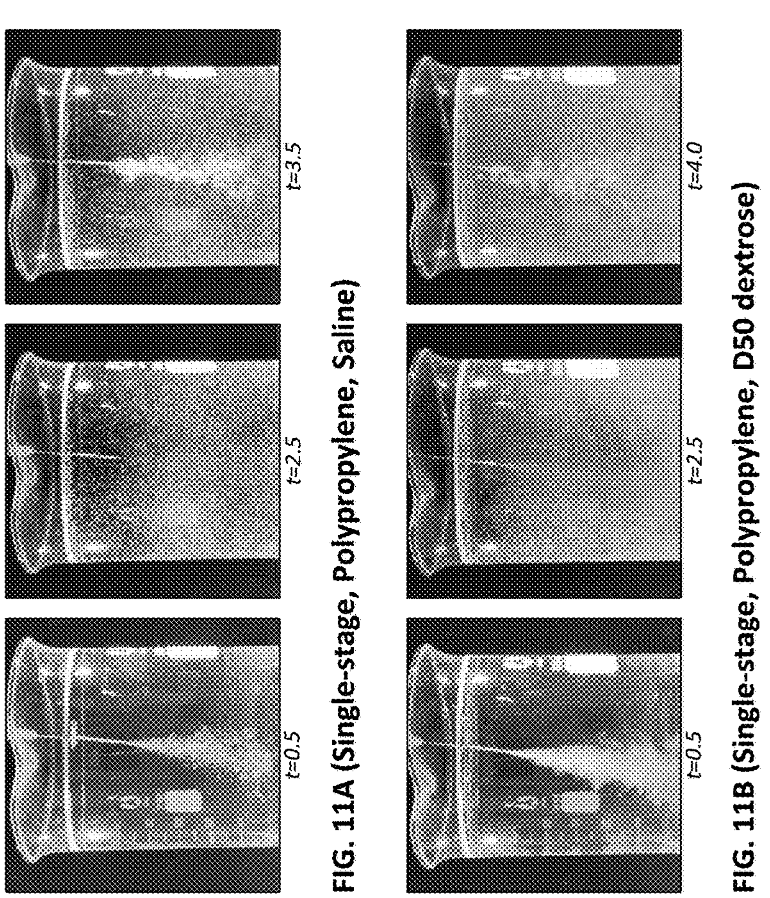
FIG. 11A (Single-stage, Polypropylene, Saline)
FIG. 11B (Single-stage, Polypropylene, D50 dextrose)
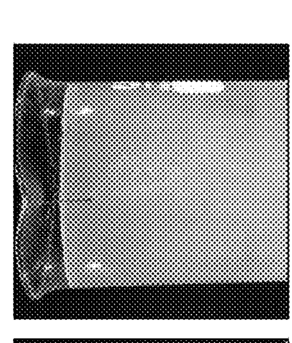
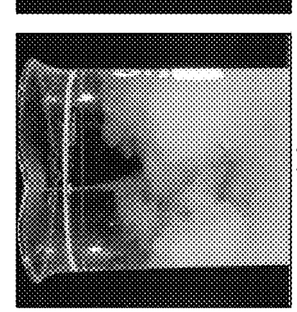
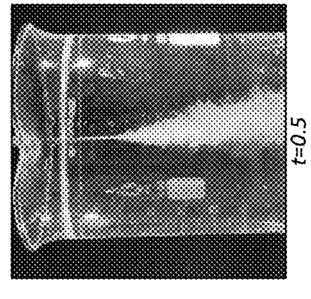
FIG. 11C (Single-stage, Polypropylene, Saline/Polysorbate)

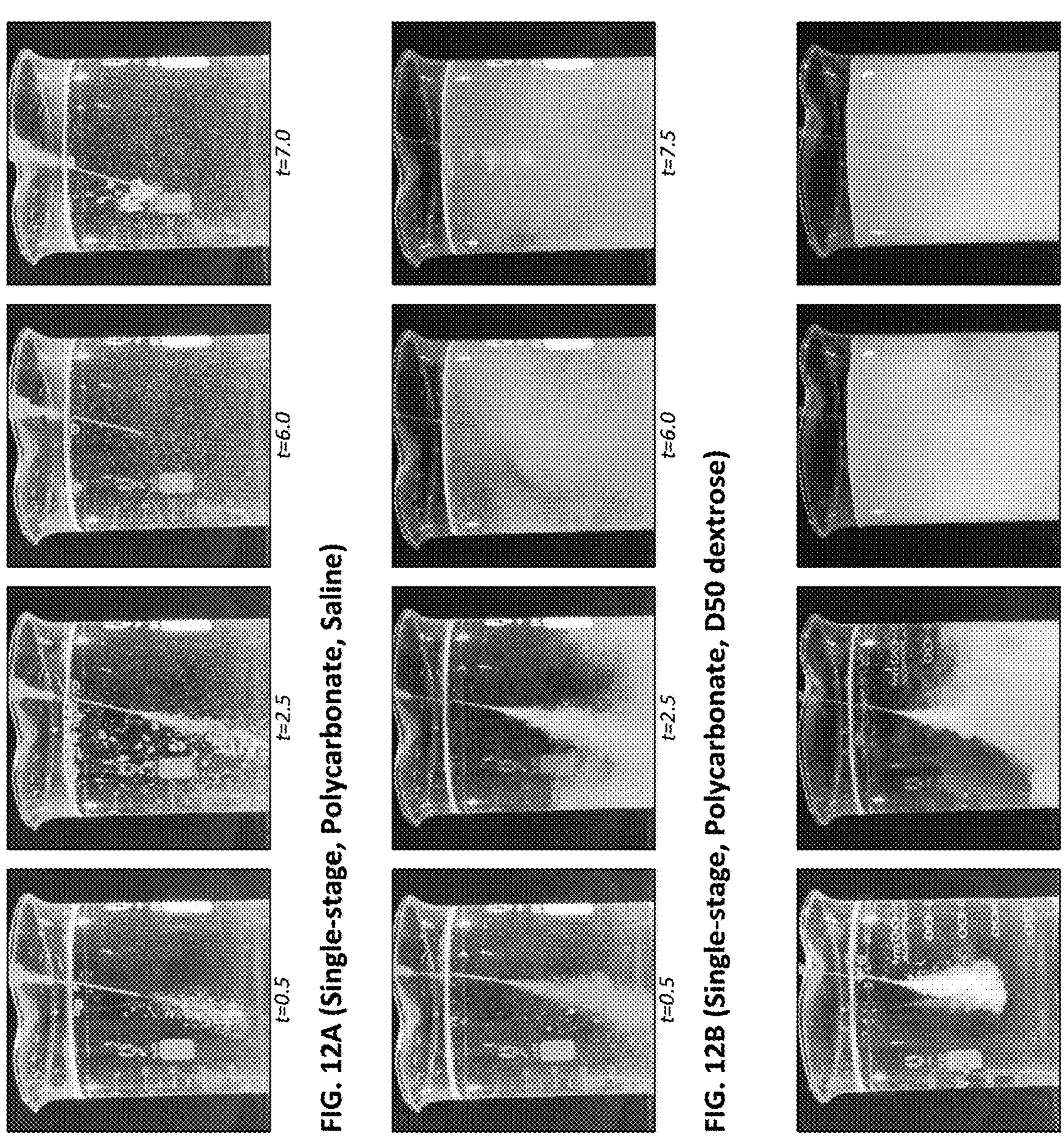
FIG. 12A (Single-stage, Polycarbonate, Saline)
FIG. 12B (Single-stage, Polycarbonate, D50 dextrose)
FIG. 12C (Single-stage, Polycarbonate, Saline/Polysorbate)

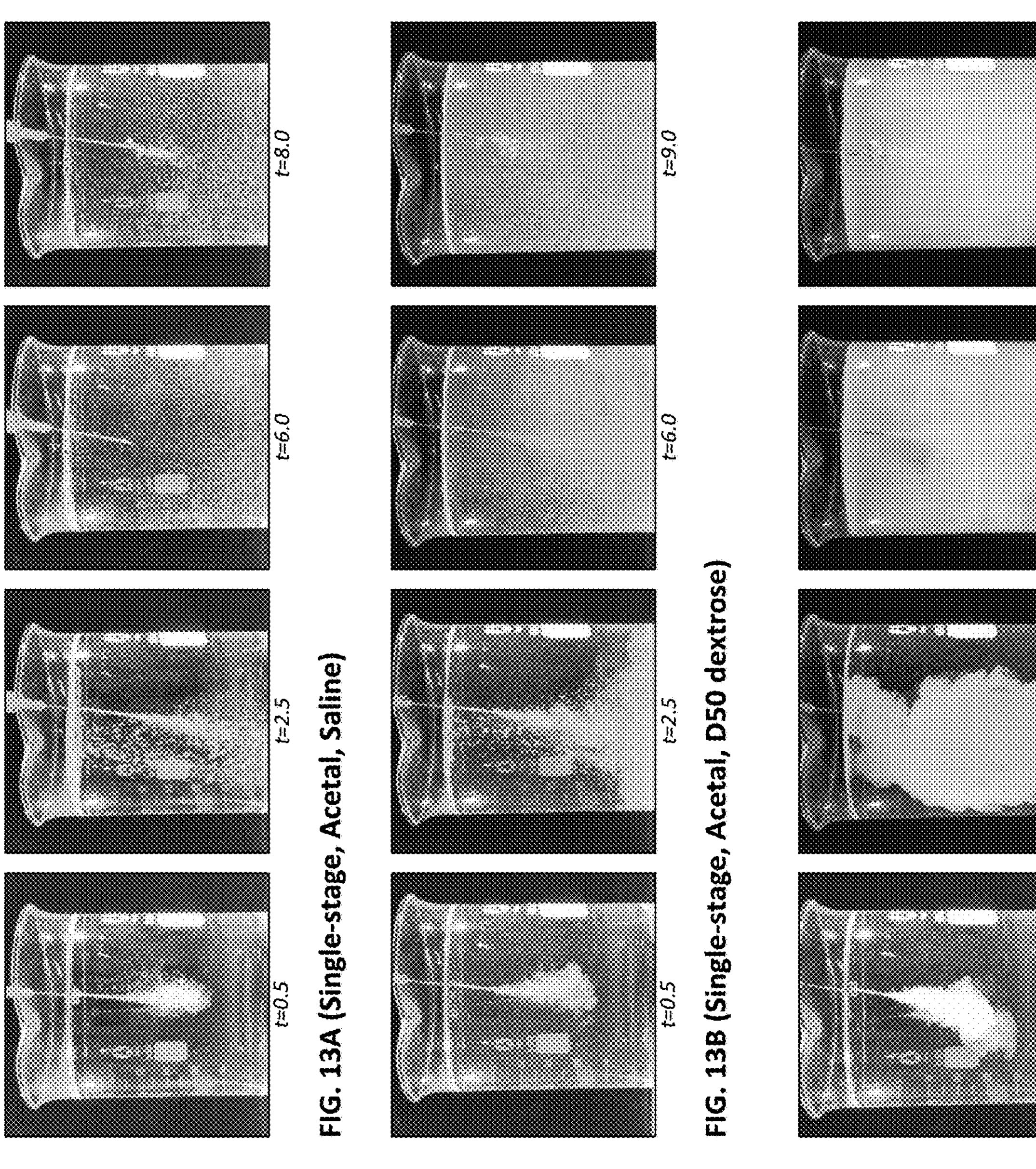
FIG. 13A (Single-stage, Acetal, Saline)
FIG. 13B (Single-stage, Acetal, D50 dextrose)
FIG. 13C (Single-stage, Acetal, Saline/Polysorbate)

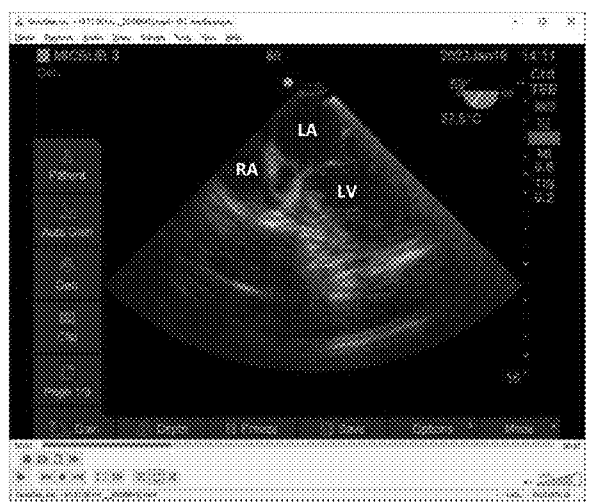
FIG. 14A
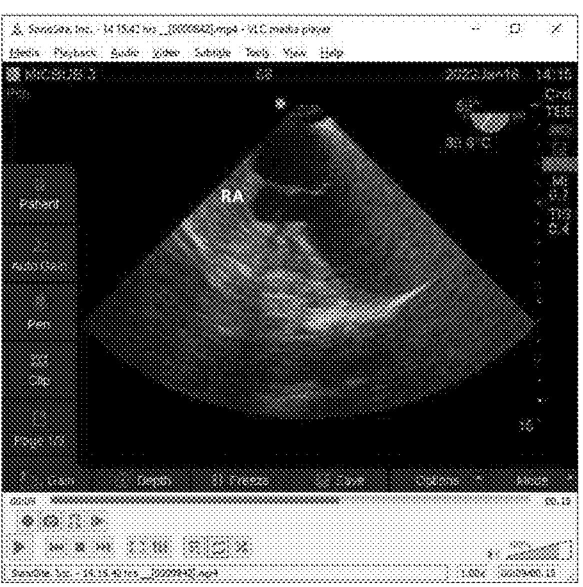
FIG. 14B

FIG. 14C
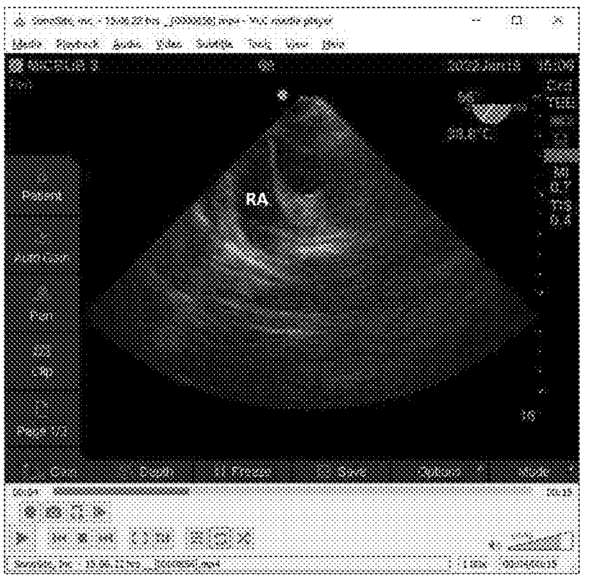
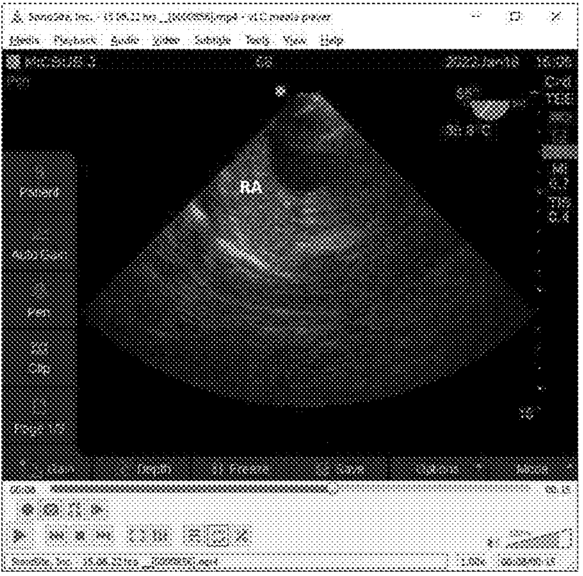
FIG. 14D

SYRINGE-BASED MICROBUBBLE GENERATOR WITH AN AERATOR

CROSS-REFERENCE TO RELATED APPLICATIONS

This application is a continuation-in-part of U.S. patent application Ser. No. 17/566,079, titled, "SYRINGE-BASED MICROBUBBLE GENERATOR WITH AN AERATOR" filed on Dec. 30, 2021, which is a continuation-in-part of U.S. application Ser. No. 17/542,386, titled "SYRINGE-BASED MICROBUBBLE GENERATOR," filed on Dec. 4, 2021, which is a continuation of U.S. patent application Ser. No. 17/158,396, titled "SYRINGE-BASED MICROBUBBLE GENERATOR," filed on Jan. 26, 2021, now U.S. Pat. No. 11,191,888. This application incorporates the entire contents of the foregoing applications herein by reference.

TECHNICAL FIELD

Various implementations relate generally to generating microbubbles for use in various diagnostic and therapeutic procedures.

BACKGROUND

Echocardiography refers to the use of ultrasound to study the heart. Echocardiography is a widely used diagnostic test in the field of cardiology and may be used in the diagnosis, management, and follow-up of patients with suspected or known heart diseases. The results from an echocardiography test may provide much helpful information, including the size and shape of the heart's components (e.g., internal chamber size quantification), pumping function, and the location and extent of any tissue damage. An echocardiogram may also give physicians other estimates of heart function, such as a calculation of the cardiac output, ejection fraction (the percentage of blood volume of the left ventricle that is pumped out with each contraction), diastolic function (how well the heart relaxes), etc.

Echocardiography may be performed in one of multiple ways. Least invasively, an ultrasound transducer may be placed on a patient's chest, and imaging may be done through the patient's chest wall, in a transthoracic echocardiogram (TTE). If a higher fidelity image is required, a more invasive transesophageal echocardiogram (TEE) may be performed, in which an ultrasound transducer disposed on a thin tube is placed down the patient's throat and into the esophagus. Because the esophagus is so close to the heart, this procedure can be employed to obtain very clear images of heart structures and valves.

During either a TTE or TEE procedure, a contrast agent may be employed to enhance the imaging of the procedure. This contrast agent may be injected into the patient's vein, such that it quickly reaches the chambers of the heart and is detected by ultrasound to give greater definition to structures of the heart. In some procedures, the contrast agent employed is a saline solution comprising tiny air bubbles, and the procedure may be referred to as an agitated saline contrast study or "bubble study."

SUMMARY

In some implementations, a device for generating microbubbles includes a syringe having a barrel and a syringe tip, a plurality of aerator components and a housing. Each aerator component may have (i) a generally cylindrical exterior body that is characterized by a longitudinal axis; (ii) an inlet end; (iii) an outlet end; (iv) a tapered outlet port at its outlet end, which tapered outlet end may be defined by an outlet diameter that is less than a body diameter corresponding to the exterior body, and a taper near the outlet end; and (v) an interior cavity comprising (A) an input port section, (B) an inlet section, (C) a throat section, (D) an outlet section, and (E) a transverse vent that fluidly couples the throat section to an area outside and adjacent to the exterior body. The housing may (x) circumferentially surround an end of the barrel and the plurality of aerator components, (y) be characterized by a longitudinal axis, (z) have an interior surface, (aa) form a circumferential gas pocket between the interior surface and the exterior body of each of the plurality of aerator components, and (bb) have a housing discharge tip. The input port section of each aerator component may be configured to accommodate the syringe tip or a tapered outlet port of one of the other aerator components in the plurality, and the housing discharge tip may be configured to accommodate the tapered outlet port of one of the plurality of aerator components, such that the syringe tip, a first aerator component, a second aerator component, and the housing can be coupled together in a coaxial manner relative to their respective longitudinal axes.

In some implementations, each of the aerator components further includes one or more alignment tabs, and the housing includes an alignment groove, such that when the syringe tip, the first aerator component, the second aerator component, and the housing are coupled together, the one or more alignment tabs and the alignment groove cooperate to radially fix the housing and each of the plurality of aerator components relative to each other.

In some implementations, a device for generating microbubbles includes a syringe having a barrel and a syringe tip that are characterized by a longitudinal axis, an aerator and a housing. The aerator may have (i) a generally cylindrical exterior body that is also characterized by a longitudinal axis; (ii) an inlet end; (iii) an outlet end; (iv) a tapered outlet port at its outlet end; and (v) an interior cavity having (A) an input port section, (B) a converging section, (C) a throat section, (D) a diverging section, (E) an outlet section, (F) a first vent that fluidly couples at least one of the throat section or the diverging section to an area outside and adjacent to the exterior body, and (G) a second vent that fluidly couples the outlet section to the area. The housing may (x) circumferentially surround an end of the barrel and the aerator, (y) be characterized by a longitudinal axis, (z) have an interior surface, (aa) form a circumferential gas pocket between the interior surface and the exterior body, and (bb) have a housing discharge tip. The input port section may be configured to accommodate the syringe tip, and the housing discharge tip may be configured to accommodate the tapered outlet port, such that the syringe tip, the aerator component, and the housing can be coupled together in a coaxial manner relative to their respective longitudinal axes.

In some implementations, the housing seals against the barrel, thereby preventing fluid communication between the area and a region exterior to the housing, except through the housing discharge tip, the first vent or the second vent. The first vent may be characterized by a first vent diameter, the second vent may be characterized by a second vent diameter, and the first vent diameter may be greater than the second vent diameter. In some implementations, the first vent diameter is about 1.0 mm, and the second vent diameter is about 0.5 mm.

In some implementations, a capacity of the barrel is about 30 mL, and a volume of the circumferential gas pocket is about 5 to 15 mL. The outlet section may be substantially cylindrical in shape. A diameter of the converging section may range between about 3.5 mm and about 0.5 mm. A diameter of the diverging section may range between about 0.65 mm and about 2.1 mm. The aerator may comprise a material having a surface energy that is greater than or equal to about 35 mN/m.

In some implementations, the device includes a body-compatible solution that is disposed in the barrel. In some implementations, the device further includes a cap that encloses a portion of the housing discharge tip and a sealing pin that occludes a portion of the interior cavity.

In some implementations, a method for generating microbubbles includes providing a microbubble generator. The microbubble generator may include (a) a syringe having a barrel and a syringe tip and being characterized by a longitudinal axis, wherein the barrel is filled with a body-compatible fluid; (b) an aerator having (i) a generally cylindrical exterior body that is also characterized by a longitudinal axis; (ii) an inlet end; (iii) an outlet end; (iv) a tapered outlet port at its outlet end; and (v) an interior cavity having (A) an input port section, (B) a converging section, (C) a throat section, (D) a diverging section, (E) an outlet section, (F) a first vent that fluidly couples at least one of the throat section or the diverging section to an area outside and adjacent to the exterior body, and (G) a second vent that fluidly couples the outlet section to the area; and (c) a housing that (x) circumferentially surrounds an end of the barrel and the aerator, (y) is characterized by a longitudinal axis, (z) has an interior surface, (aa) forms a circumferential gas pocket between the interior surface and the exterior body, and (bb) has a housing discharge tip. The input port section may be configured to accommodate the syringe tip, and the housing discharge tip may be configured to accommodate the tapered outlet port, such that the syringe tip, the aerator component, and the housing can be coupled together in a coaxial manner relative to their respective longitudinal axes.

The method may further include coupling the housing discharge tip to an intravenous line disposed in a patient undergoing a procedure. The method may further include generating microbubbles by forcing the body-compatible fluid out of the syringe, through the interior cavity, and through the housing discharge tip.

In some implementations, the aerator comprises a material having a solid surface energy of about 35 mN/m or more. In some implementations, the aerator comprises polycarbonate. In some implementations, the aerator comprises one of polycarbonate, polymethacrylate, polyvinyl chloride, polyamide, acrylonitrile butadiene styrene, acetal or polyethylene terephthalate glycol.

In some implementations, the body-compatible fluid comprises dextrose. In some implementations, the body-compatible fluid comprises saline and polysorbate. In some implementations, the body-compatible fluid comprises saline and dextrose or a body-compatible surfactant.

BRIEF DESCRIPTION OF THE DRAWINGS

FIG. 6A is a perspective cross-sectional view of another exemplary microbubble generator.

FIG. 6B is a perspective view of an aerator component that may be included in the exemplary microbubble generator of FIG. 6A.

FIG. 6C is a perspective cross-sectional view of the aerator component of FIG. 6B.

FIG. 6D is a side view of the aerator component of FIG. 6B.

FIG. 6E is a side cross section of the aerator component of FIG. 6B.

FIG. 6F is a perspective cross-sectional view of a plurality of aerator components that may be coupled together and included in the exemplary microbubble generator of FIG. 6A.

FIGS. 9A-9C illustrate microbubbles formed with an exemplary multi-stage polypropylene aerator and saline, dextrose and saline with polysorbate, respectively.

FIGS. 10A-10C illustrate microbubbles formed with an exemplary multi-stage polycarbonate aerator and saline, dextrose and saline with polysorbate, respectively.

FIGS. 11A-11C illustrate microbubbles formed with an exemplary single-stage polypropylene aerator and saline, dextrose and saline with polysorbate, respectively.

FIGS. 12A-12C illustrate microbubbles formed with an exemplary single-stage polycarbonate aerator and saline, dextrose and saline with polysorbate, respectively.

FIGS. 13A-13C illustrate microbubbles formed with an exemplary single-stage acetal aerator and saline, dextrose and saline with polysorbate, respectively.

FIG. 14A illustrates a TEE procedure in a porcine model in which microbubbles were produced using a current standard-of-care procedure.

FIG. 14B illustrates a TEE procedure in a porcine model in which microbubbles were produced using an exemplary aerator with saline and polysorbate at a 0.1% concentration.

FIG. 14C illustrates a TEE procedure in a porcine model in which microbubbles were produced using an exemplary aerator with saline and polysorbate at a 0.01% concentration.

FIG. 14D illustrates a TEE procedure in a porcine model in which microbubbles were produced using an exemplary aerator with saline and polysorbate at a 0.005% concentration.

DETAILED DESCRIPTION

Agitated saline contrast studies (or "bubble studies") are a useful adjunct to many ultrasound examinations, particularly cardiac ultrasound (echocardiography). Injection of agitated saline into a vein combined with echocardiography is a validated method to detect shunts which may be within the heart such as a patent foramen ovale (PFO) or an atrial septal defect (ASD)—two types of holes in the heart—or external to the heart (e.g., in the lungs) known as pulmonary arteriovenous malformations (pAVM). Agitated saline can also be used with echocardiography to confirm catheter placement in fluid around the heart (pericardiocentesis), detect anomalous connections within the heart, visualize the right side of the heart and accentuate right sided blood flow for the purpose of quantitation.

Agitated saline contrast echocardiography takes advantage of the increased reflection that results when ultrasound waves meet a liquid/gas interface. This allows for visualization of otherwise poorly reflective areas such as fluid-filled cavities by the ultrasound machine. Applications in which this has been clinically useful include echocardiography where agitated saline can be used to define the structural integrity of the interatrial septum or infer the presence of a transpulmonary shunt. Agitated saline can also be combined with Doppler echocardiography to assess blood flow through the tricuspid valve. An alternative method to detect atrial defects uses ultrasound of the brain vessels (transcranial Doppler) to detect bubbles that have crossed from the right heart to the left heart and entered the cerebral circulation.

At present, it may be difficult to generate agitated saline for these studies, and this can result in varying levels of quality and safety. Current bubble studies may have considerable variability in the amount, size, and quantity of bubbles generated. Such imprecise mixtures of saline and air can result in risk to patients and false-negative studies. In addition, few individuals may be properly trained to safely perform bubble studies. The productivity of an echocardiography lab may be substantially slowed by this lack of trained personnel; and even trained personnel who do not routinely perform agitated saline studies may be reluctant to do so because of concerns about comfort or safety of the procedure.

Described herein are devices and methods for producing bubbles (e.g., for an ultrasound-based bubble study). Advantages of the devices and methods described herein may include the production of more uniform and consistently dimensioned bubbles with minimal training. This may result in greater patient safety and comfort as well as studies with improved diagnostic benefit.

Figure 1:
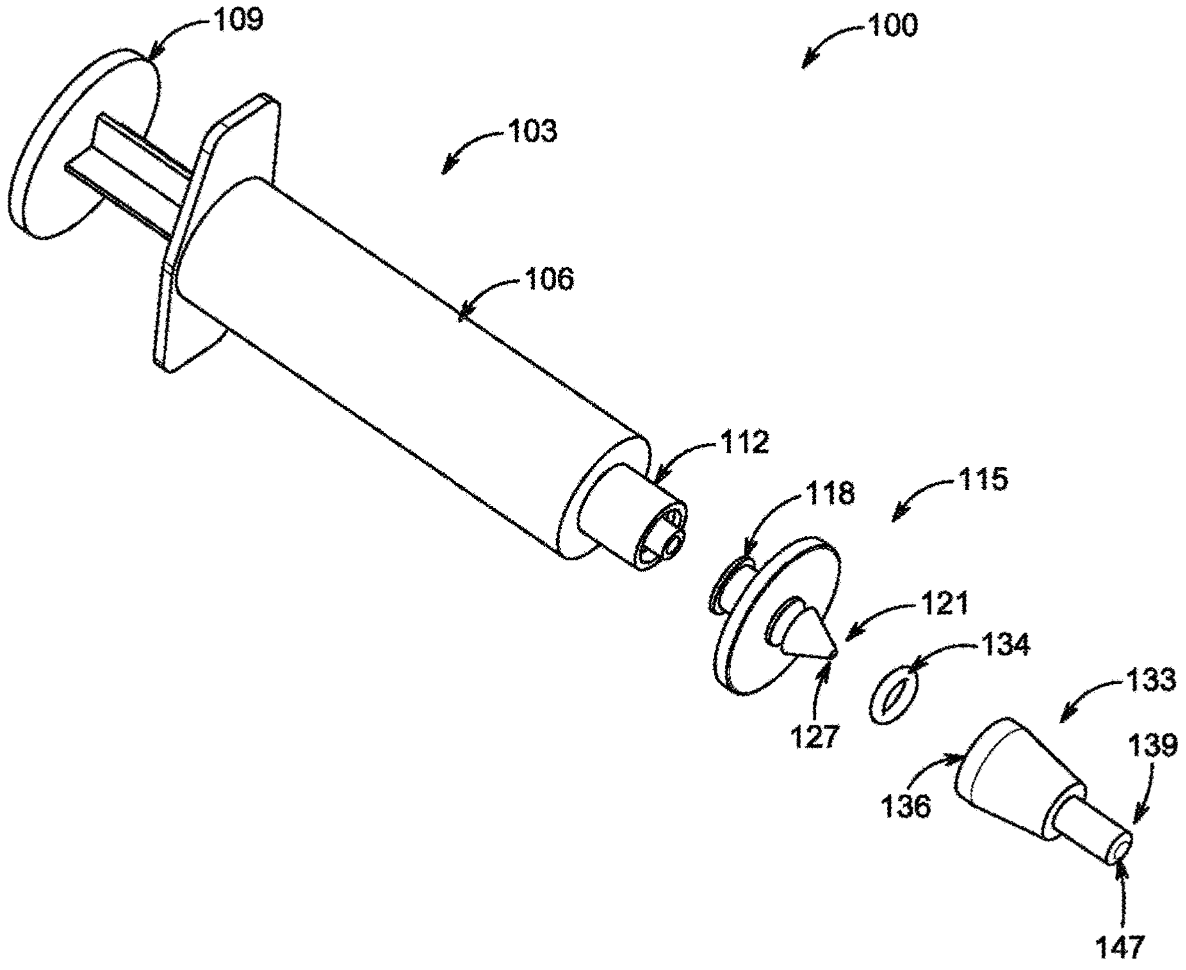
FIG. 1 is an exploded perspective view of an exemplary microbubble generator.

FIG. 1 is an exploded perspective view of an exemplary microbubble generator 100, according to one implementation. As shown, the microbubble generator 100 includes a syringe 103, a converging nozzle 115, and an aerator 133. In operation, the microbubble generator 100 can be coupled to an intravenous (IV) line disposed in a patient undergoing a procedure (e.g., a diagnostic bubble study), and the microbubble generator 100 can be employed to generate microbubbles as a contrast agent.

In some implementations, the syringe 103 portion of the microbubble generator 100 is a standard medical-grade syringe (e.g., 1 mL, 2 mL, 3 mL, 5 mL, 10 mL, 20 mL) having a barrel 106, plunger 109 and tip 112. The syringe 103 may be pre-filled with saline or another solution that is suitable for intravenous injection, which can provide a vehicle for microbubbles generated by the microbubble generator 100 to be delivered to a target region of a patient's body. The tip 112 can include a Luer lock connector suitable for coupling to needles, catheters, IV lines, etc.

Saline is referenced with respect to various implementations. In some implementations, this could be "NSS," or 0.9% normal saline solution; in other implementations, "45NS," or 0.45% normal saline may be used; in other implementations, phosphate-buffered saline (PBS) may be used. In still other implementations, liquids other than saline may be used, such as dextrose in water solution (e.g., "D5W," or 5% dextrose in water; "D10W," or 10% dextrose in water; "D50," or 50% dextrose in water) or other solutions commonly used in intravenous applications at sites that are suitable for diagnostic studies or therapeutic procedures.

The converging nozzle 115, in the implementation shown, has a coupling end 118 that is configured to engage the tip 112 of the syringe 103. In some implementations, the coupling end 118 includes mating Luer lock threads to facilitate a twist-on engagement with the syringe 103. Opposite the coupling end 118 is a converging tip 121. An interior channel 127, which will be described in greater detail with reference to the following figures, is configured to fluidly couple an interior of the syringe 103 to the aerator 133.

The aerator 133, as shown, includes a retention end 136 that is configured to mechanically mate with the converging nozzle 115; and a discharge end 139. In some implementations, the aerator 133 can be coupled to the converging nozzle 115 via a compression-fit coupling facilitated by an O-ring 134 and grooves in the converging nozzle 115 and aerator 133. A discharge channel 147 fluidly couples the interior channel 127 of the converging nozzle 115 to a discharge end 139, which can be configured to engage a catheter or IV port or line used in a bubble study.

In FIG. 1, the syringe 103, converging nozzle 115 and aerator 133 are shown as separate components. In other implementations, however, one or more components may have other arrangements. For example, the converging nozzle 115 and aerator 133 may be ultrasonically welded together, joined with adhesive, snap-fit, etc.; and the converging nozzle 115 or a singular converging nozzle/aerator structure could be coupled to the syringe 103 in one of the foregoing ways or co-molded with and as part of the syringe 103. Additional detail of the exemplary syringe 103, converging nozzle 115 and aerator 133 is now provided with reference to FIGS. 2A, 2B and 2C.

Figure 2A:
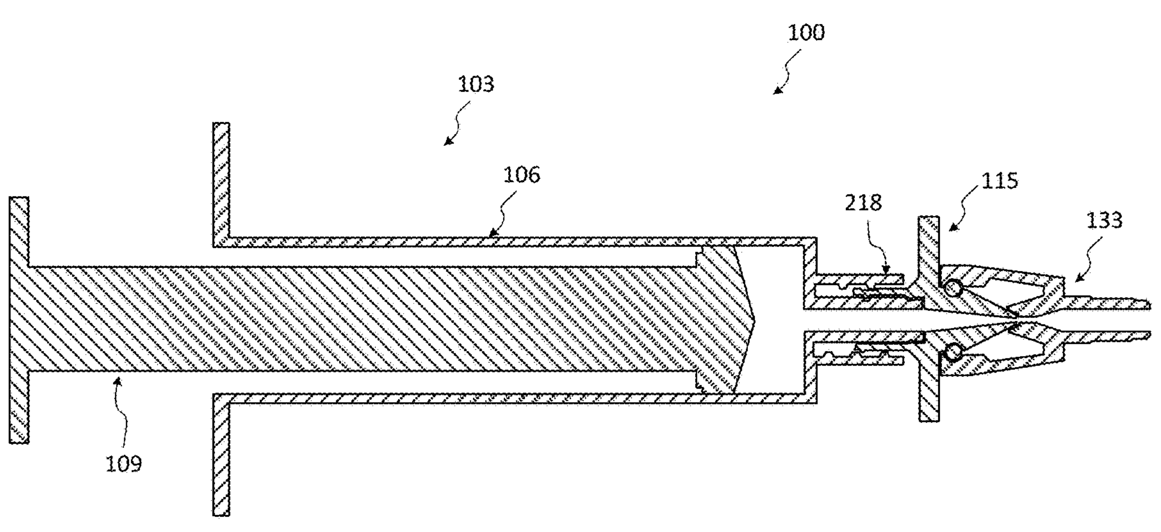
FIG. 2A is a longitudinal cross section of an exemplary syringe, converging nozzle, and aerator, as they are assembled, in one implementation.

FIG. 2A illustrates a longitudinal cross-section of the syringe 103, converging nozzle 115 and aerator 133, as they could be assembled in some implementations. As shown, the converging nozzle 115 is disposed on the syringe 103 via a Luer lock fitting 218, and the aerator 133 is compression-fit onto the converging nozzle 115 by an O-ring and corresponding grooves in each of the converging nozzle 115 and aerator 133 (see FIG. 2B for detail). In other implementations, connections maybe made differently. For example, other threaded or press-fit connections may replace Luer lock fittings. Similarly, the O-ring and grooves could be replaced by a threaded, adhesive-based or welded connection.

Figure 2B:
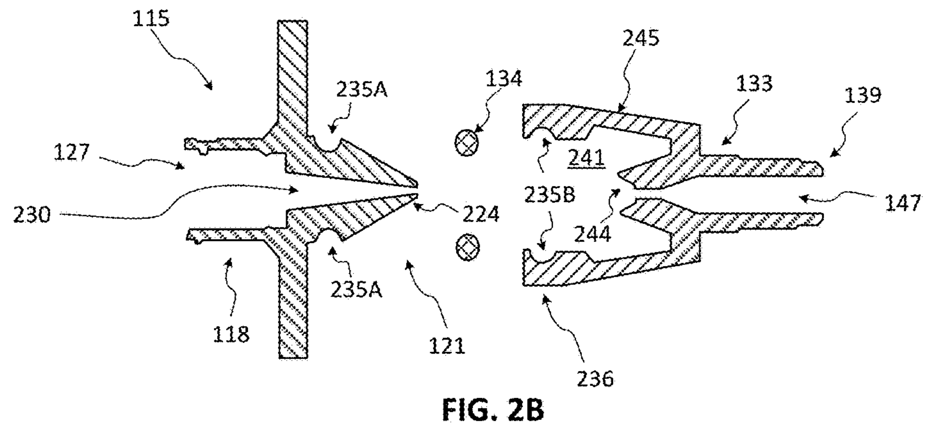
FIG. 2B is a longitudinal cross section of the converging nozzle, O-ring, and aerator shown in FIG. 2A.

FIG. 2B illustrates an exemplary longitudinal cross section of the converging nozzle 115, O-ring 134, and aerator 133. The interior channel 127 fluidly couples to an interior of the mating syringe 103 (see FIGS. 1, 2A) and a throat 230—a portion of the interior channel 127 whose diameter progressively decreases. In operation, the progressively decreasing diameter of the throat 230 changes dynamics of fluid flowing from the syringe 103 and through the converging nozzle 115, as will be described with reference to FIG. 2C.

As shown, the converging nozzle 115 includes grooves 235A for receiving the O-ring 134 and facilitating a compression-fit coupling; and the aerator 133 includes corresponding grooves 235B for the same purpose. This structure allows the O-ring 134 to be slipped into the grooves 235A, and for the retention end 236 of the aerator 133 to be slid over the converging tip 121 and for the grooves 235B to engage and be retained by the O-ring 134. In such an implementation, the O-ring 134 may be made of an elastic material that has sufficient elasticity and compressibility to facilitate engagement of the converging nozzle 115 and aerator 133, and sufficient resilience to securely couple the converging nozzle 115 and aerator 133 once the grooves 235A and 235B of these components 115 and 133 are aligned as described. In some implementations, the O-ring 134 and grooves 235A and 235B may provide an air-tight, sterile seal.

The converging nozzle 115 further includes an external mating surface 224 at the converging tip 121, which is configured to mechanically fit adjacent to a corresponding circumferential lip 244 on the aerator 133. In some implementations, the circumferential lip 244 circumferentially envelopes the external mating surface 224 and abuts the external mating surface 224 at least at one point; in other implementations, the circumferential lip 244 and external mating surface 224 are disposed adjacent and in close proximity to each other. When the converging nozzle 115 and aerator 133 are coupled (e.g., by the grooves 235A and 235B and O-ring 134), the external mating surface 224 and circumferential lip 244 align and facilitate fluid coupling between the interior fluid channel 127 and throat 230, and the discharge channel 147. In some implementations, specific dimensions and geometries of the external mating surface 224 and circumferential lip 244 further facilitate passage of air into the discharge channel 147, from an interior air chamber 241, which is formed by the outer wall 245 of the aerator 133—as will be further described with reference to FIG. 2C.

Figure 2C:
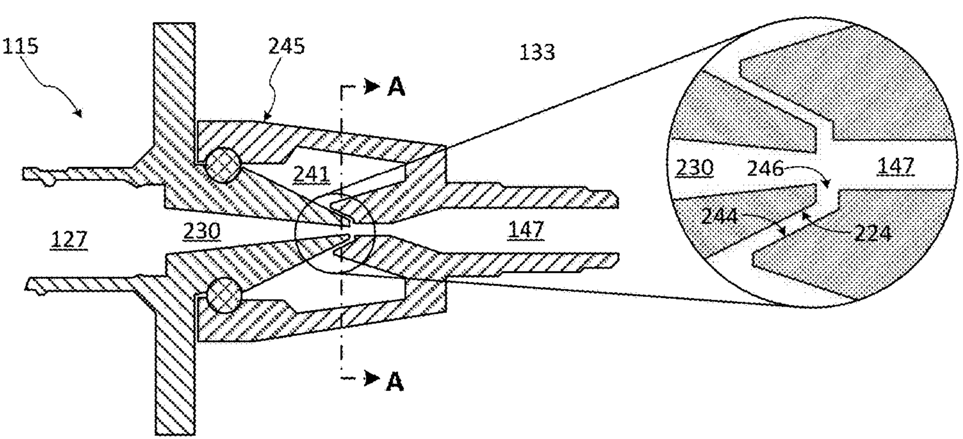
FIG. 2C is another longitudinal cross section of the converging nozzle, O-ring and aerator shown in FIG. 2A.

FIG. 2C is a longitudinal cross section of the converging nozzle 115 and aerator 133, shown in a coupled configuration, and a magnified view of a portion of that cross section. As shown, the interior air chamber 241 is formed by the outer wall 245 of the aerator. A small fluid coupling exists between this interior air chamber 241 and the passageway formed by the interior channel 127, throat 230 and discharge channel 147—specifically by an air channel 246 (see magnified inset) that is configured to exist between the exterior mating surface 224 and the circumferential lip 244. This air channel 246 allows air or other gas in the interior air chamber 241 to be drawn into the aforementioned passageway (throat 230 and discharge channel 147—referred to as the "230/147 passageway"). In addition, this air channel 246 may permit some fluid that is passing through the 230/147 passageway to enter the interior air chamber 241, thereby displacing some of the air there and increasing the pressure in the interior air chamber 241 (e.g., in cases in which there may be a non-negligible back pressure at the discharge channel 147).

Figure 2D:
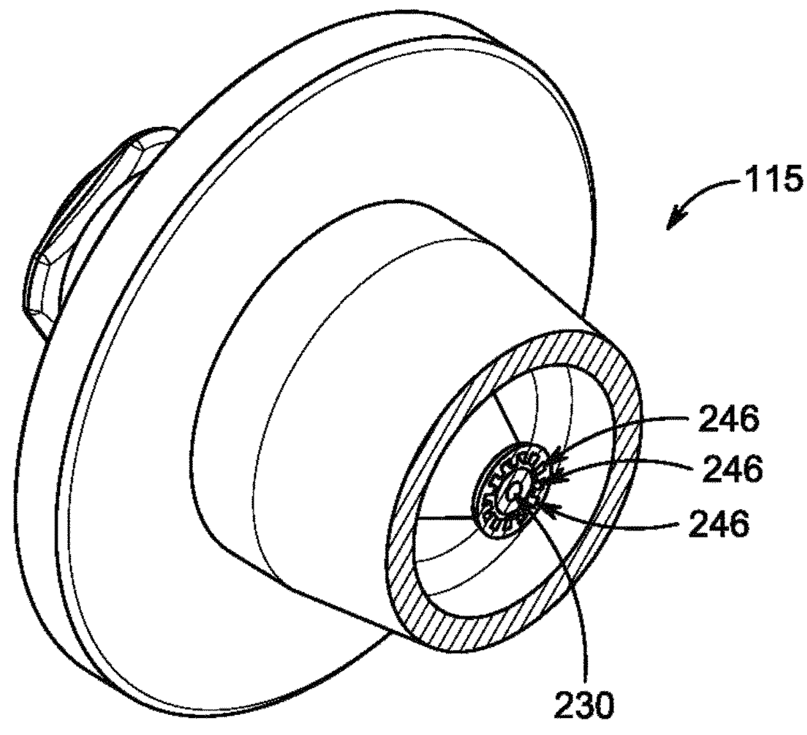
FIG. 2D is a perspective, cross-sectional view of the configuration shown in FIG. 2C.

FIG. 2D is a perspective, cross-sectional view of the converging nozzle 115 shown in FIG. 2C, with the cross section taken along section line A-A (shown in FIG. 2C). FIG. 2D illustrates the air channel 246 (or series of air channels 246) that fluidly couple the interior air chamber 241 to the throat 230-discharge channel 147 passageway. Visible in FIG. 2D is the throat 230 itself, in the center of the converging nozzle 115, as well as a series of air channels 246 that are disposed radially about throat.

In some implementations, the exterior mating surface 224 and circumferential lip 244 (see FIG. 2C) are in mechanical contact and provide a fluid seal, except at the air channels 246. That is, in such implementations, a fluid coupling between the interior air chamber 241 and the 230/147 passageway only exists at the air channels 246. In some implementations, fewer air channels 246 are provided than shown—for example, some implementations may only include one, two, three or four air channels 246.

Referring back to FIG. 2C, dimensions and geometries of the air channels 246 may be configured to facilitate passage of air from the interior air chamber 241 into the 230/147 passageway only when certain pressure differentials exist therebetween. For example, some implementations may include air channels 246 with very small dimensions and with geometries that promote greater surface tension of any liquid that is disposed in the air channels 246. Specific contours of either or both of the exterior mating surface 224 and the circumferential lip 244 may further promote an increased surface tension of liquid in the air channels 246, to, for example, promote communication of air (and correspondingly, formation of microbubbles) in certain scenarios. Surface treatments to either or both of the exterior mating surface 224 and the circumferential lip 244 (e.g., hydrophobic or hydrophilic coatings) may be employed to further control communication of air or other gas from the interior air chamber 241 to the 230-147 passageway.

In some implementations, a vent (not shown) between the interior air chamber 141 and the exterior of the aerator 133 may be provided to enable more air to be drawn into the fluid than may otherwise be possible. In other implementations, a port or valve (not shown) may be provided to facilitate coupling of an exterior air supply for a similar purpose. In still other implementations, a valve (e.g., a reducing valve—not shown) may be provided to allow fluid to be drained from the air chamber 241 and again be replaced with air—for example, to facilitate an equilibrium relative to back pressure, and to enable the microbubble generator 100 to "recharge" its ability to generate microbubbles.

Figure 2E:
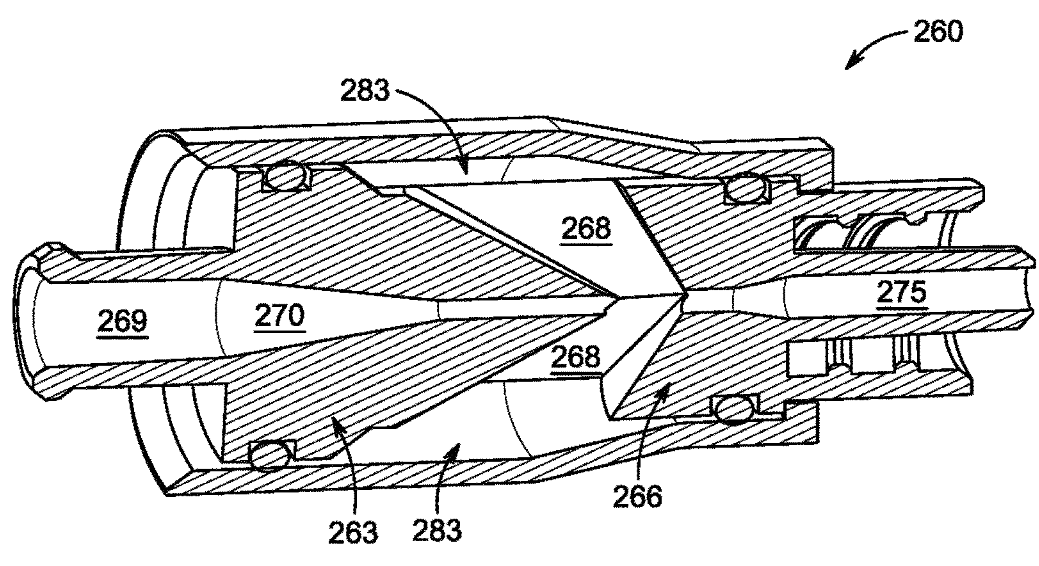
FIG. 2E is a perspective cross-sectional view of another exemplary converging nozzle and aerator.
Figure 2F:
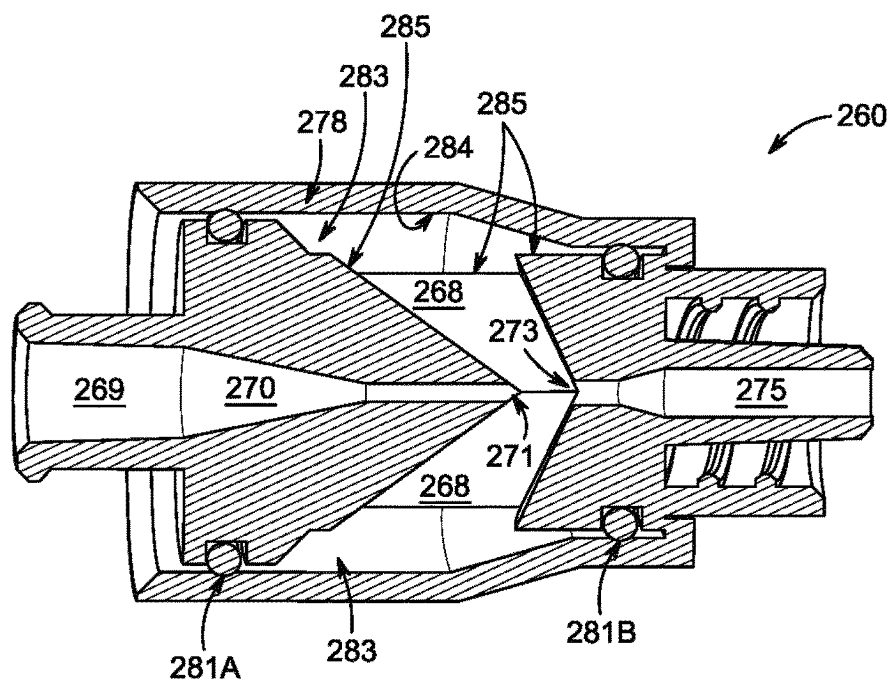
FIG. 2F is a longitudinal cross-sectional view of the converging nozzle and aerator shown in FIG. 2E.

FIG. 2E illustrates a perspective cross-sectional view of an exemplary implementation 260 of a unitary converging nozzle 263 and aerator 266; and FIG. 2F illustrates a longitudinal cross-section of the same device 260. As shown in this implementation, the converging nozzle 263 and aerator 266 are fabricated as a unitary component (e.g., co-molded), rather than as two separate components. In such a configuration, it may be possible to precisely configure dimensions of one or more air channels 268 and their alignment to a stream of fluid traveling from an interior channel 269, through a section 270 having a progressively decreasing diameter (e.g., a "Venturi section"), out an outlet 271, into an inlet 273 of the aerator 266 and through and out a discharge channel 275.

As shown, the exemplary device 260 includes a housing 278 that surrounds the unitary converging nozzle 263 and aerator 266. In some implementations, as shown, the housing 278 can be sealed to the converging nozzle 263 and aerator 266 by O-rings 281A and 281B. In such implementations, an air chamber 283 is formed (e.g., by an interior surface 284 of the housing 278 and an exterior surface 285 of the unitary component that includes the converging nozzle 263 and aerator 266). When the O-rings 281A and 281B form an airtight and liquid-tight seal (of the air chamber 283, isolating the air chamber 283 from a region exterior to the housing 278 from ingress or egress of gas or liquid via any path other than through the one or more air channels), air (or other gas) in the air chamber 283 can be drawn into a stream of liquid passing through the device 260, in the form of microbubbles.

In some implementations, the exemplary device 260 can operate to produce microbubbles even in the presence of not-insignificant back pressure at the discharge channel 275. Specifically, in the presence of back pressure at the discharge channel 275 (with a robust seal provided by O-rings 281A and 281B), fluid may pass through the interior channel 269, section 270 and into the discharge channel 275. However, no significant volume of fluid may flow out of the discharge channel 275 (e.g., into a downstream intravenous or needle-based system associated with a therapeutic or diagnostic procedure) until pressure is equalized between the device 260 and the back pressure. That is, rather than flowing out of the discharge channel 275, the fluid may initially flow through the air channels 268 and into the interior air chamber 283. Such fluid may displace the air in the air chamber 283, causing an increase in pressure in the air chamber 283.

Once this air pressure increases to the level of the back pressure, fluid may then flow through the device 260, out of the discharge channel 275, and into a connected patient diagnostic or therapeutic system (not shown). In this phase of operation, where the pressure inside the air chamber 283 is nearly equal to the back pressure seen at the discharge channel 275, some air from the air chamber 283 may be drawn into the fluid stream, in the form of microbubbles—via an aspiration effect caused by the pressure drop in the fluid stream itself that is brought about by the increase in speed of flow of that fluid through the Venturi section 270.

Over time, the aspiration of air into the fluid stream may cause the pressure in the air chamber 283 to again drop below a back pressure seen at the discharge channel 275. At this point, some additional fluid may enter the air chamber 283, again displacing air and increasing the pressure inside the air chamber 283. Once equilibrium is reestablished, or nearly reestablished (e.g., within some small percentage, given the dynamic nature of the system, turbulence of the fluid, dynamically varying back pressure, variation in speed of fluid, etc.), air may again be aspirated into the fluid stream in the form of microbubbles.

In some implementations, a one-way reducing valve (not shown) may be provided between the air chamber 283 and an exterior of the housing 278, to enable fluid to be periodically drained from the air chamber 283. Allowing some fluid to be drained from the air chamber 283 may allow, in some implementations, air to be continuously available for aspiration into the fluid stream. In such an implementation, microbubbles may be produced and delivered out of the discharge channel 275 for as long as incoming fluid is supplied through the interior channel 269.

In the implementation shown in FIGS. 2E and 2F, dimensions, geometries and surface treatments (e.g., hydrophobic or hydrophilic coatings) of the air channels 268, the outlet 271 (or interior channel 269 or section 270), the inlet 273 or the discharge channel 275 may be configured to facilitate creation of microbubbles having a specific average size or range of sizes (e.g., an average diameter of less than 2 μm; an average diameter of between about 5 μm and about 10 μm; an average diameter of about 40 μm or less; an average diameter of about 100 μm or less). Such implementations may employ dimensions, geometries or surface treatments to produce regions of turbulent or laminar flow that entrap or aspirate air in a particular manner. In other implementations, specific dimensions, geometries or surface treatments may be employed to create microbubbles with surface tensions or charges that minimize coalescence of microbubbles after they are generated.

Figures 3A, 3B, 3C:
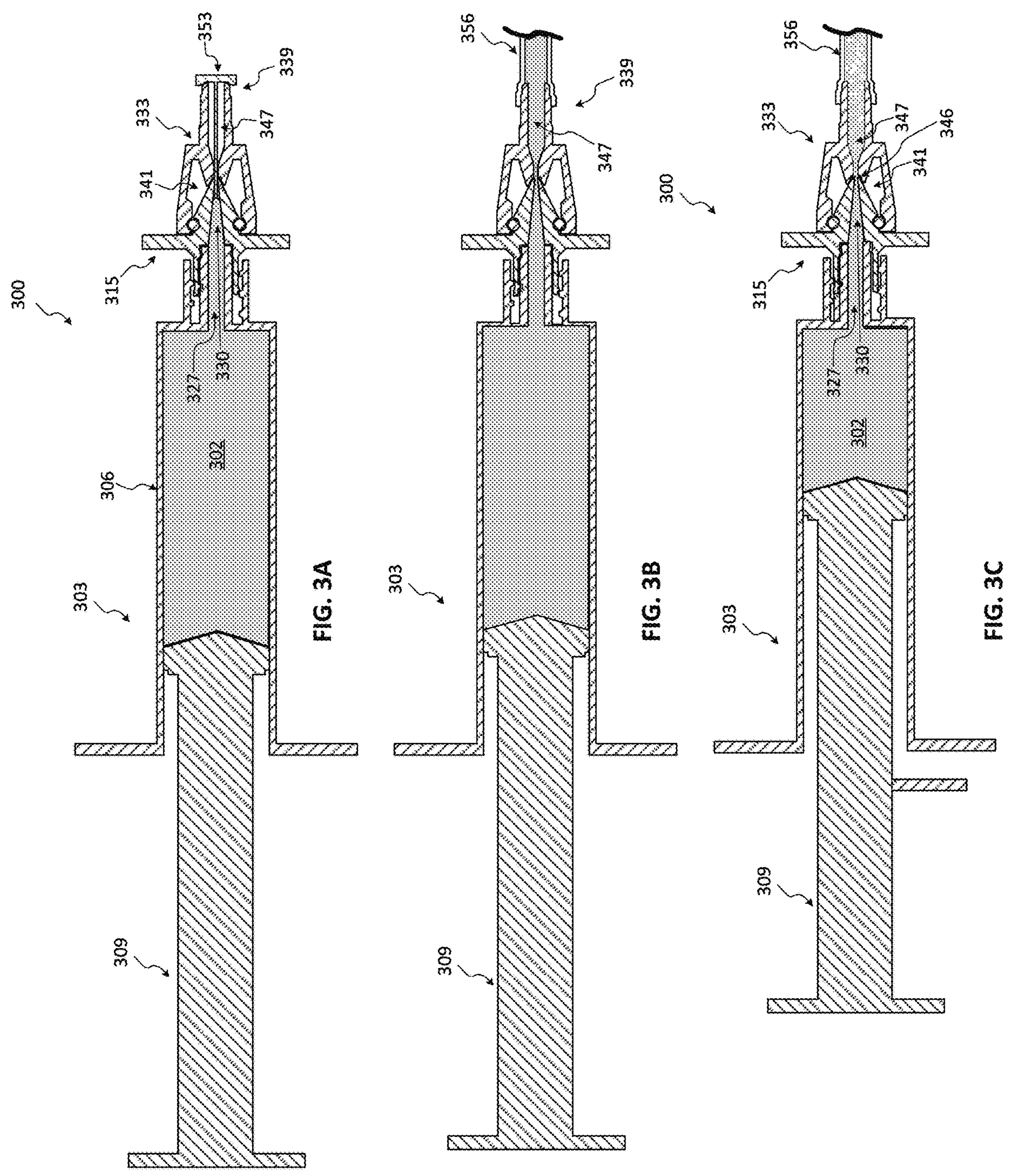
FIGS. 3A, 3B and 3C depict operation of an exemplary microbubble generator.

Operation of an overall exemplary microbubble generator 300 are now described with respect to FIGS. 3A, 3B and 3C, in one implementation. As shown in FIG. 3A, a microbubble generator 300 that includes a syringe 303, a converging nozzle 315 and an aerator 333 may be prefilled with a saline solution. That is, saline (or another suitable solution) may be prefilled in an interior 302 of the barrel 306 of the syringe portion 303. To preserve the sterile nature of the saline, and to prevent fluid ingress into an interior chamber 341 of the aerator portion 333, a sealing pin 353 may be provided to seal the saline in the syringe 303, to seal the interior channel 327 and throat 330 of the converging nozzle 315 and to isolate the channel 327 from the interior chamber 341. In operation, such a pin 353 may be removed immediately prior to use of the microbubble generator 300.

The pin 353 may be made of a corrosion-resistant metal or resilient elastic material that seals off the tip of the throat 330 and a discharge channel 347. The pin 353 may be adhesively sealed to the discharge end 339 of the aerator, such that some amount of twisting or pulling force is required by a user to dislodge the pin 353 prior to use of the microbubble generator 300. Such an adhesive seal may further protect the sterile nature of the microbubble generator 300, particularly at the discharge end 339.

In some implementations, the pin 353 may be replaced with an internal membrane (not shown) that retains the saline (or other body-compatible fluid) in the interior 302 of the syringe or in the interior 302 of the syringe and the throat 330 of the converging nozzle 315. In such implementations, a user may be required to depress the plunger 309 in order to generate an internal pressure that is sufficient to overcome the holding force of such a membrane. In some implementations, an internal membrane (not shown) may be configured to be broken when the converging nozzle 315 is affixed to the syringe 303 (e.g., in implementations in which the components are provided separately).

However the contents of the syringe are sealed prior to use, the appropriate seal can be released and the plunger 309 can be depressed slightly to flush microbubble generator 300—as depicted in FIG. 3B. In some instances, this can be done prior to the discharge end 339 being coupled to IV tubing 356 or another connection that may be made to a system used to diagnose or treat a patient (e.g., a needle, catheter, or other apparatus disposed in the patient (not shown)). In other instances, the discharge end 339 may be coupled to IV tubing 356 first, such that the tubing can also be flushed during this initial process.

FIG. 3C depicts the process by which the microbubble generator 300 can generate microbubbles, in one implementation. In particular, after necessary seals are removed, and the microbubble generator 300 is flushed and coupled to a downstream IV system 356 associated with a patient undergoing a diagnostic or therapeutic procedure, the plunger 309 can be further depressed to force fluid from the interior 302 of the syringe 303, into the interior channel 327. In the interior channel 327, the pressure of the fluid is relatively high, and its speed is relatively low (proportional to a speed at which the plunger is depressed). The progressively decreasing diameter of the throat 230 causes the speed of the fluid to increase there, thereby lowering its fluid pressure (through the Venturi effect). This lower pressure of the fluid at the throat 330 draws air into the fluid path traveling from the throat 330 to the discharge channel 347, specifically from the interior chamber 341, via one or more air channels 346—thereby forming microbubbles.

In some implementations, the geometry, dimensions and/or surface treatment of the material forming the air channels 346 is correlated to microbubble size. Thus, in such implementations, configuration of converging nozzle 315 and aerator 333 can cause microbubbles to be created having different sizes and characteristics. In some implementations, microbubbles having a diameter of approximately 5 μm may be created; in other implementations, microbubbles having a diameter of approximately 10 μm or less may be created; in other implementations, microbubbles having a diameter of about 1-2 μm or less may be created; in other implementations, microbubbles having a diameter of about 40 μm may be created; in other implementations, microbubbles having a diameter up to about 100 μm may be created.

Different sized microbubbles may have different purposes in diagnostic or therapeutic procedures. For example, in certain diagnostic heart procedures, it may be advantageous to create microbubbles of approximately 5 μm to approximately 10 μm in average diameter. As used herein, "about" or "approximately" or "substantially" may mean within 1%, or 5%, or 10%, or 20%, or 50% of a nominal value; and "average" may mean that a significant number (e.g., 25%, 50%, 75%, 80%, 85%, 90%, 95%) of microbubbles have this diameter, or in some implementations, have a diameter that is within one or two standard deviations of the specified diameter. As another example, in diagnosing certain pulmonary conditions, it may be advantageous to create smaller-diameter microbubbles (e.g., 1-2 μm or less). In some implementations, microbubble size may be correlated with coalescence properties of the microbubbles. For example, surface tension and charge of microbubbles of specific sizes (in certain solutions, or in the blood) may inhibit their coalescence; and minimizing such coalescence of microbubbles may be advantageous (e.g., to minimize risk of an air embolism).

In some implementations, it may be advantageous to generate microbubbles of varying sizes. For example, in a procedure to diagnose the existence of a defect in the septum of a patient's heart, it may be advantageous to initially look for the presence of a septum defect with smaller microbubbles; then shift to larger microbubbles to determine whether a closure procedure is warranted. To facilitate procedures in which it may be advantageous to employ microbubbles of varying sizes, multiple microbubble generators may be employed; and in some implementations, they may be coupled together in advance.

Figure 4:
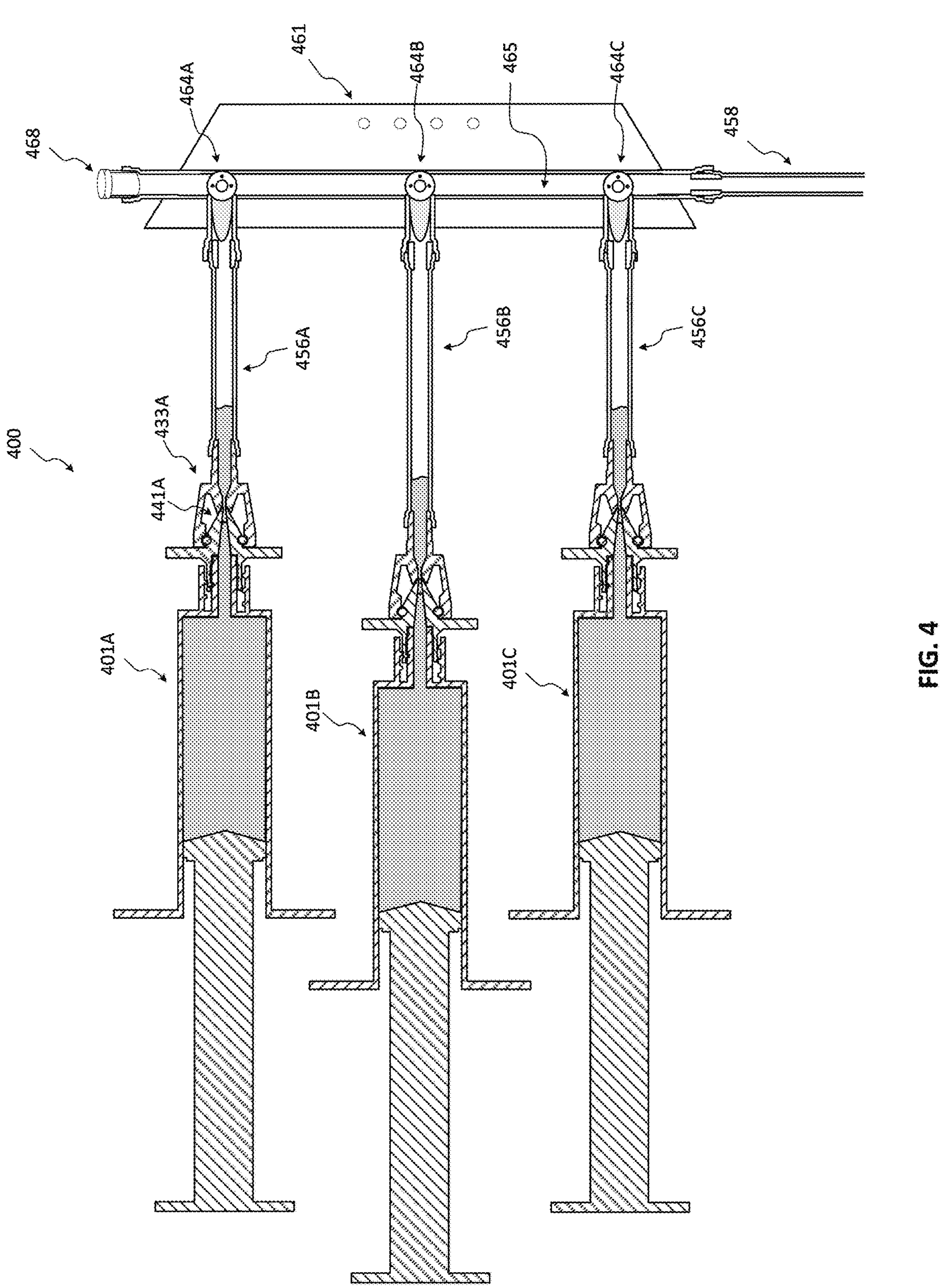
FIG. 4 illustrates an exemplary microbubble generating system.

FIG. 4 illustrates an exemplary microbubble generating system 400 that employs multiple microbubble generators 401A, 401B and 401C. As shown, each microbubble generator 401A, 401B and 401C can be coupled to a manifold 461 by corresponding fluid lines 456A, 456B and 456C. The manifold can include multi-way valves 464A, 464B and 464C that couple or isolate each fluid line to a main line 465 of the manifold 461; and that main line 465 of the manifold 461 can be coupled to an IV line 458 that is associated with a patient undergoing a diagnostic or therapeutic procedure. In this manner, individual microbubble generators 401A, 401B or 401C can be alternately coupled to the IV line 458 to generate diagnostic or therapeutic microbubbles; or, multiple microbubble generators 401A, 401B or 401C can be simultaneously connected to facilitate delivery of a large volume of fluid with minimal manipulation of valves. Some implementations employ three-way stopcocks 464A, 464B and 464C, as shown, to isolate or fluidly couple one, two or three paths. Other implementations may employ different valve arrangements.

In some implementations, each microbubble generator 401A, 401B or 401C, in a microbubble generating system 400 may be similarly configured to generate microbubbles of the same size. Such implementations may be employed to generate a larger volume of microbubbles, over a longer period of time than would be otherwise possible with a single microbubble generator. In other implementations, each microbubble generator 401A, 401B and 401C may be configured to generate microbubbles of different sizes. For example, microbubble generator 401A may be configured to generate microbubbles having an approximate diameter of 5 μm; microbubble generator 401B may be configured to generate microbubbles having an approximate diameter of 1 μm; and microbubble generator 401C may be configured to generate microbubbles having an approximate diameter of 10 μm. In this manner, complex diagnostic procedures requiring microbubbles of various sizes may be performed with minimal change in equipment.

The exemplary manifold 461 may include a port 468 for flushing out the manifold and/or overall system 400. In some implementations, each microbubble generator 401A, 401B and 401C may have an internal membrane to isolate fluid within a corresponding syringe barrel or syringe barrel/converging nozzle; and discharge channels of each microbubble generator and the manifold itself may be flushed and prefilled with fluid prior to a procedure being performed, through the port 468.

In other implementations, the system 400 may be packaged in a manner in which the syringes, tubing and manifold are all pre-filled with fluid, such that a final connection between a main manifold line 465 and patient IV tubing 458 need be made at the time of a procedure. In such implementations, internal membranes may still be employed in individual microbubble generators 401A, 401B and 401C to prevent egress of fluid into interior air chambers of an aerator component (e.g., air chamber 441A in aerator 433A).

The exemplary system 400 is shown with three microbubble generators 401A, 401B and 401C; but other numbers of microbubble generators could be included—such as, for example, two, four, or five. The microbubble generators 401A, 401B and 401C are shown coupled to the manifold 461 with tubing 456A, 456B, and 456C. In some implementations, various components of the system 400 may be provided and coupled together immediately prior to a patient procedure.

Various implementations described herein may be employed to generate microbubbles for various diagnostic and therapeutic studies. Many such studies involve the human circulatory system. Thus, for reference, portions of a human circulatory system are now briefly described.

Figure 5:
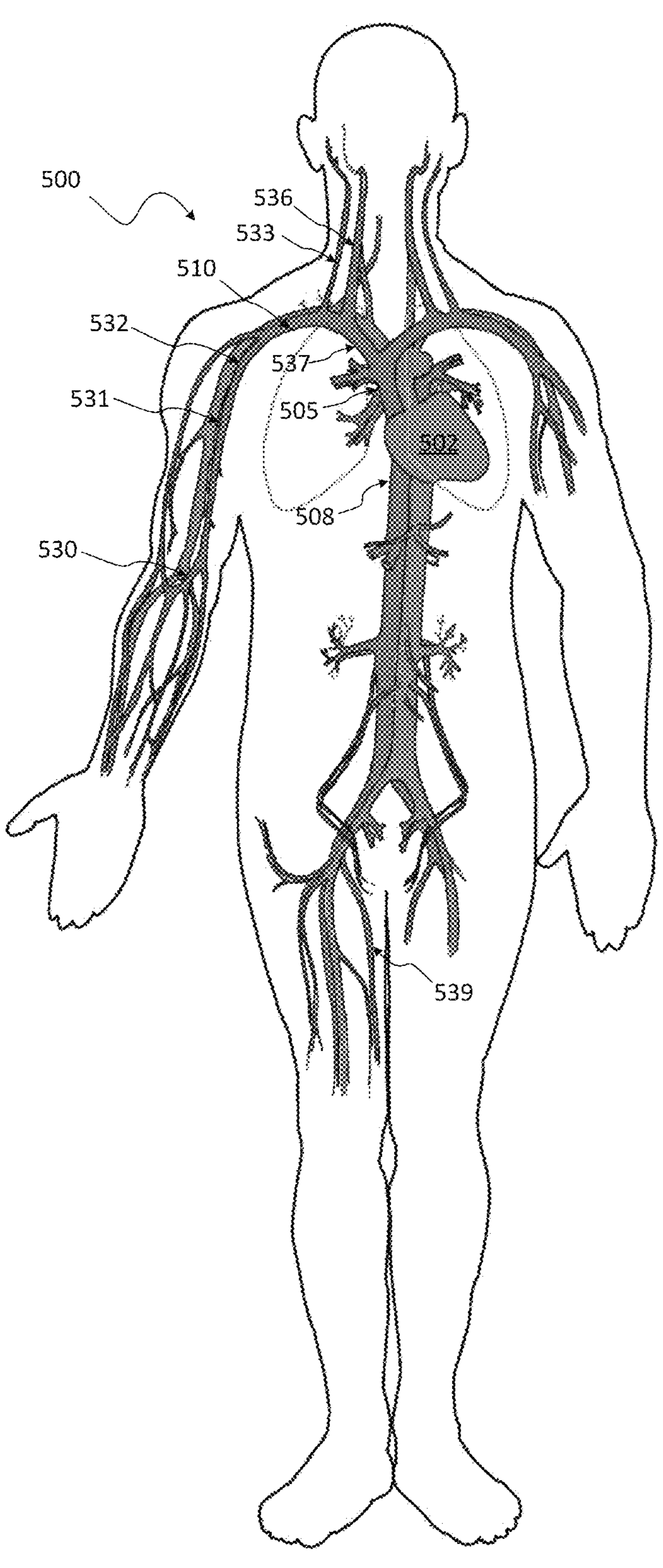
FIG. 5 illustrates a portion of an overall human circulatory system.

FIG. 5 illustrates a portion of an overall human circulatory system 500. At its core, is the heart 502, and a system of arteries that extend from the heart, and veins that return to the heart. Blood is returned to the heart 502 from throughout the body via the vena cava, which is divided into the superior vena cava 505, which collects blood from the upper portion of the body, and the inferior vena cava 508, which collects blood from the lower portion of the body. Blood flows through the superior vena cava 505 and inferior cava 108 on its way to the right atrium.

To facilitate studies whereby microbubbles are to be introduced into the heart and lungs, one must get the bubbles into the venous system and ultimately into the superior vena cava 505 or inferior vena cava 508. With reference to FIG. 5, there are several common access points through which microbubbles can be introduced. Common among them is intravenous introduction of bubbles via the median cubital vein 530 of the right arm. From here, blood flows through the basilic vein 531, axillary vein 532, subclavian vein 510, brachiocephalic vein 537 and into the superior vena cava 505.

Alternative paths to the superior vena cava 513 are the external jugular vein 533 or internal jugular vein 536, both of which drain into a brachiocephalic vein 537 prior to reaching the superior vena cava 505. An alternative route includes the femoral vein 539, which flows into the inferior vena cava 508. Other routes to the superior vena cava 505 and inferior vena cava 508 are possible.

FIG. 6A is a perspective cross-sectional view of another exemplary microbubble generator 600. As shown, the exemplary microbubble generator 600 includes a syringe 603 having a barrel 606, a plunger 609, and a syringe tip 612. In some implementations, as shown, the syringe tip 612 includes a Luer lock 613 or other fitting.

A plurality of aerator components 616*a*, 616*b* and 616*c* may be coupled to the syringe tip 612, and a housing 619 may circumferentially surround an end of the barrel 606 and the plurality of aerator components 616*a*, 616*b* and 616*c*. The housing 619 may have a longitudinal axis 622, which, in some implementations, aligns coaxially with a longitudinal axis 623 of the syringe 603 and longitudinal axes of the aerator components 616*a*, 616*b*, and 616*c*.

The housing 619 has an interior surface 625 and a discharge tip 628. In some implementations, the housing 619 is configured to fluidly seal against the barrel 606, and the plurality of aerator components 616*a*, 616*b*, and 616*c* may be sealed against each other, to the syringe tip 612, and to the discharge tip 628, such that any fluid that is ejected from the syringe 603 (e.g., by a user of the syringe 603 depressing the plunger 609) is ejected through the syringe tip 612, into an interior channel 673 (see FIG. 6F) of each of the aerator components 616*a*, 616*b* and 616*c*, through the discharge tip 628. A circumferential gas pocket 631 may be created by the interior surface 625; the plurality of aerator components 616*a*, 616*b* and 616*c*; the syringe tip 612; and the discharge tip 628. In some implementations, the circumferential gas pocket 631 comprises at least approximately 10% of the volume of the corresponding syringe barrel 606; in other implementations, the circumferential gas pocket 631 comprises approximately 30-35% of the volume of the corresponding syringe barrel 606 (e.g., 3-3.5 mL for a 10 mL syringe); in still other implementations, the circumferential gas pocket 631 comprises 50% or more of the volume of the corresponding syringe barrel 606.

Regardless of the precise volume of the circumferential gas pocket 631 relative to the volume of the syringe barrel 606, one advantage is that this overall volume of the circumferential gas pocket 631 may be precisely controlled to a fail-safe value. Specifically, in medical applications, such as those described herein, this precise value may be set to a level that would prevent harm to a patient—even if all gas or air in the circumferential gas pocket 631 were directly injected into the patient (e.g., through some device failure). Such a safety feature that is inherent in the design of implementations described herein may be absent from other implementations (e.g., current standard-of-care implementations, such as the one described below in Example 16)—where a volume of air or gas that is mixed with a body-compatible fluid may be controlled only by a specific clinician performing a corresponding procedure (possibly resulting in significant variation from one clinician to another with implementations other than those described herein).

FIG. 6B is a perspective view of an aerator component 616*b* that may be included in the exemplary microbubble generator 600 of FIG. 6A. As shown the aerator component 616*b* has an exterior body 630, which, in some implementations is cylindrical and characterized by a longitudinal axis 624. One or more alignment tabs, such as alignment tab 632, may protrude from the exterior body 630; and such alignment tab 632 may be configured to interface with one or more alignment grooves 633 in the housing 619 (see FIG. 6A)—such that when the aerator components 616*a*, 616*b* and 616*c* and housing 619 are coupled together, the one or more alignment tabs 632 and the one or more alignment grooves 633 cooperate to radially fix the housing and each of the plurality of aerator components relative to each other.

As indicated above, when disposed in the microbubble generator 600, the longitudinal axis 624 of the aerator component 616*b* may align coaxially with the longitudinal axis 622 of the housing 619 and the longitudinal axis 623 of the syringe 603. The aerator component 616*b* has an inlet end 634 and an outlet end 637. As will be described in more detail with reference to FIGS. 6D and 6E, the aerator component 616*b* may include a tapered output port 640 and a transverse vent hole 643.

FIG. 6C is a perspective cross-sectional view of the aerator component 616*b*; FIG. 6D illustrates a side view of the aerator component 616*b*; and FIG. 6E illustrates a side cross section of the aerator component 616*b*. As illustrated in FIG. 6D, the tapered output port 640 may have a diameter 646 that is less than a diameter 649 of the exterior body 630, as well as a taper 652 that narrows the diameter 646 from its start at the exterior body 630 to its distal end.

With reference to FIG. 6E, in the implementation shown, the aerator component 616*b* includes an interior cavity 655 that has four discrete sections—an input port section 658, an inlet section 661, a throat section 664, and an outlet section 667. The input port section 658 is configured to receive a tapered output port of another aerator component (e.g., the tapered output port 640 of aerator component 616*b*) or of the syringe tip 612—that is, the input port section 658 may have a diameter 670 that is only slightly larger than the diameter 646 of the tapered output port 640, and that diameter 670 may decrease from outside to inside the input port section 658, corresponding to the taper 652 of the tapered output port 640.

As shown, the inlet section 661 has a progressively decreasing diameter that constricts flow of a gas or liquid through the aerator component 616*b* as that gas or liquid flows from the input port section 658 to a subsequent throat section 664. As described above with respect to other implementations, this constriction of flow increases the corresponding velocity of the gas or liquid and lowers its pressure. This lowering of pressure allows gas or liquid in the circumferential air pocket 631 (see FIG. 6A) to be drawn into the flow, through the transverse vent hole 643, in the throat section 664. In some implementations, the progressively decreasing diameter ranges from about 3.5 mm to about 0.5 mm.

In some implementations, as shown, an outlet section 667 follows the throat section 664. In the outlet section 667, a diameter of the interior cavity 655 increases from the throat section 664 toward the tapered output port 640. In some implementations, the increasing diameter of the outlet section 667 ranges from about 0.5 mm to 3.5; more preferentially, the diameter may range from about 0.65 mm to about 2.1 mm.

In some implementations, a boundary between the inlet section 661 and throat section 664 may be rounded and/or smooth (e.g., to minimize turbulence). In some implementations, the throat section 664 may have a slight taper (e.g., to facilitate a clean molding process). In some implementations, a boundary between the throat section 664 and outlet section 667 may by rounded and/or smooth (e.g., to minimize turbulence). In some implementations, various surfaces and boundaries may have a rough surface treatment, or edges may be sharp, rather than rounded or smooth (e.g., to increase turbulence).

FIG. 6F is a perspective cross-sectional view of a plurality 616 of aerator components 616*a*, 616*b* and 616*c* that may be coupled together and included in the exemplary microbubble generator 600. As shown, each component 616*a*, 616*b* and 616*c* is tightly coupled to the next, such that a channel 673 is formed from the input port section of the aerator component 616*a* to the outlet section of the aerator component 616*c*. In some implementations, the channel 673 is fluid-tight from end-to-end, except at the transverse vent holes in each aerator component 616*a*, 616*b*, and 616*c*—that is, each aerator component may be tightly sealed to the next, such that fluid (e.g., liquid or gas) cannot leak out of the channel 673 at the intersection of the tapered output port of one aerator component and the input port section of another aerator component.

As depicted in FIG. 6F, some variation may exist in the diameter of each throat section 664*a*, 664*b* or 664*c* in the plurality 616 of aerator components. That is, the diameter of throat section 664*c* of aerator component 616*c* may be larger than the diameter of throat section 664*b*, which may be larger than the diameter of throat section 664*a*. Similarly, there may be variation in the diameters of the transverse vent holes 643*a*, 643*b* and 643*c*. In some implementations, diameters of the throat sections 664*a*, 664*b* and 664*c* may range from 0.4 mm or less to 2.0 mm or more. For example, one implementation may include aerator components with diameters of 0.45 mm, 2 mm and 2 mm; another implementation may include aerator components with diameters of 0.45 mm, 1 mm and 2 mm; yet another implementation may include aerator components with diameters of 1 mm, 1 mm and 2 mm. In some implementations, it may be advantageous to arrange aerators such that diameters are increasing from proximal end (e.g., the syringe end) to the distal end; in other implementations, a different arrangement may be advantageous.

In some implementations, the diameters of transverse vent holes 643*a*, 643*b* and 643*c* may range from 0.3 mm or less to 1.0 mm or more. For example, in some implementations, the proximal-most vent hole 643*a* may be approximately 1.0 mm, and the distal-most vent hole 643*c* may be approximately 0.6 mm; in other implementations, the proximal-most vent hole 643*a* may be approximately 0.3 mm, and the distal-most vent hole 643*c* may be approximately 0.6 mm.

Figure 6G:
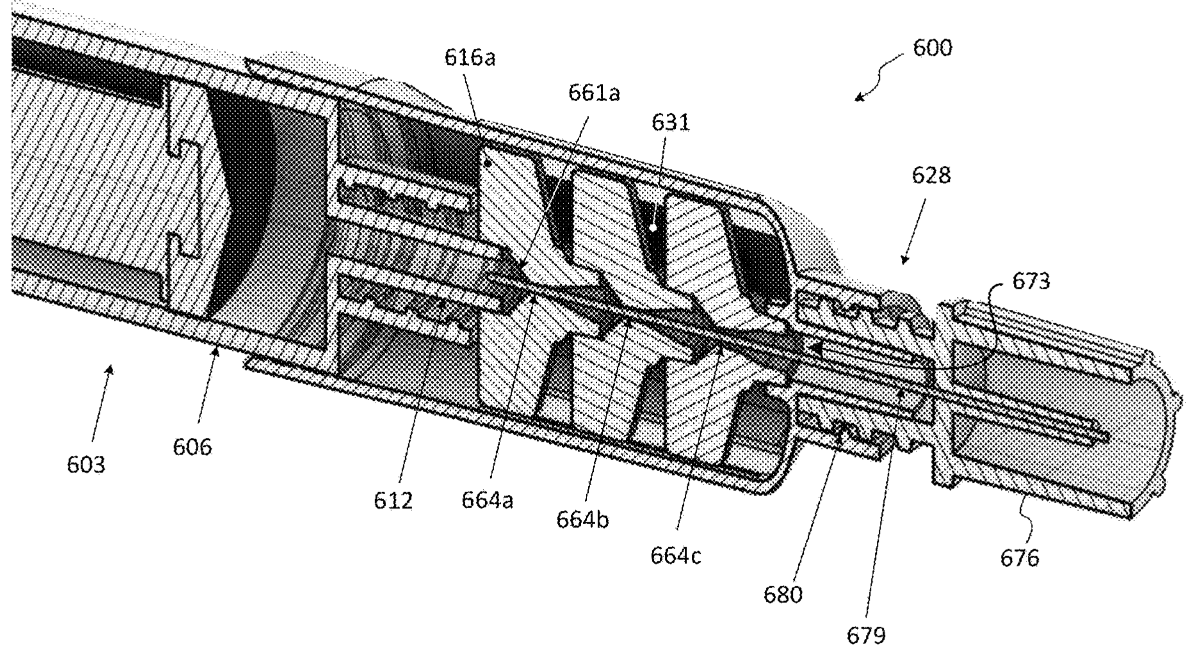
FIG. 6G is a perspective cross-sectional view of the exemplary microbubble generator of FIG. 6A, including a cap and sealing pin.

FIG. 6G is a perspective cross-sectional view of the exemplary microbubble generator 600, including a cap 676 and sealing pin 679. In some implementations, as shown, the cap 676 is threaded to engage with a Luer lock 680 or other threaded fitting at the discharge tip 628. The cap 676 may include a sealing pin 679, which, in some implementations, is configured to seal off the smallest-diameter throat section (e.g., throat section 664*a*, as shown). In such implementations, the cap 676 may seal off the channel 673 and the circumferential gas pocket 631 (through the transverse vent holes (not visible in FIG. 6G)); and the sealing pin may seal off the throat 664*a*, thereby sealing off the inlet section 661*a* of aerator 616*a* and everything fluidly coupled thereto (e.g., an interior of the syringe tip 612 and of the barrel 606). In these implementations, the cap 676 and sealing pin 679 may maintain sterility of the contents of the syringe 603 and may prevent liquid or gas in the syringe 603 from leaking into the circumferential gas pocket 631 before the cap 676 and sealing pin 679 are removed.

Figure 7A:
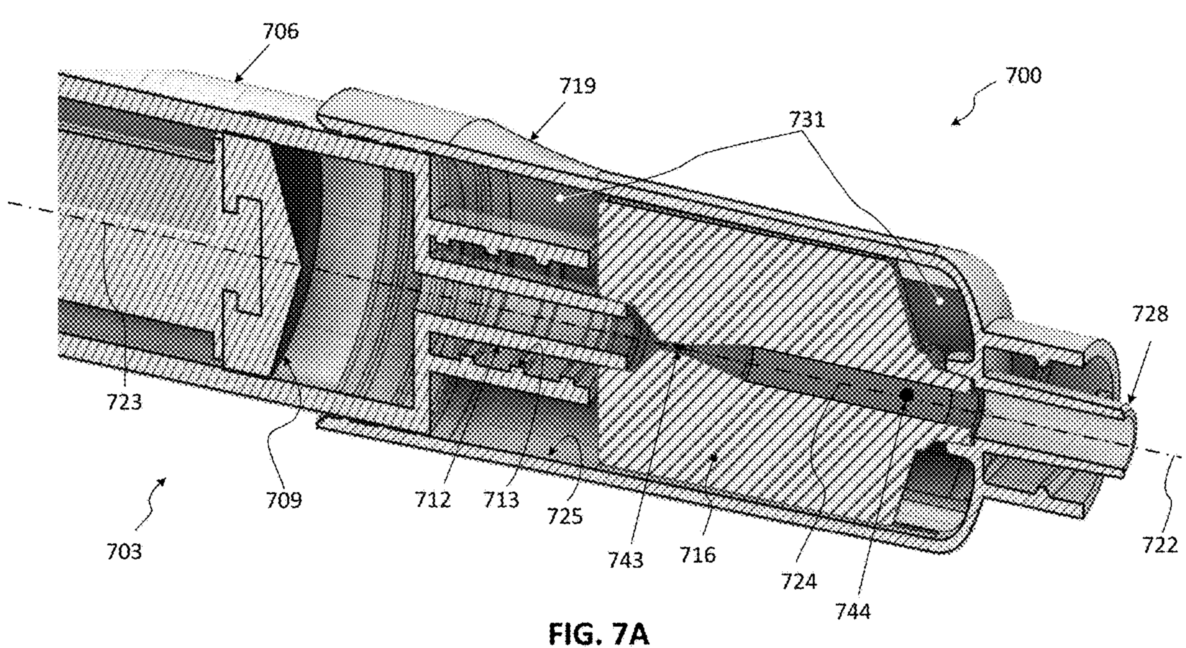
FIG. 7A is a perspective cross-sectional view of another exemplary microbubble generator.

FIG. 7A is a perspective cross-sectional view of another exemplary microbubble generator 700. As shown, the exemplary microbubble generator 700 includes a syringe 703 having a barrel 706, a plunger 709, and a syringe tip 712. The syringe tip 712 may include a Luer lock fitting 713 having corresponding threads.

An aerator 716 may be coupled to the syringe tip 712, and a housing 719 may circumferentially surround an end of the barrel 706 and the aerator 716. The housing 719 may have a longitudinal axis 722, which, in some implementations, aligns coaxially with a longitudinal axis 723 of the syringe 703 and a longitudinal axis 724 of the aerator 716.

As shown, the housing 719 has an interior surface 725 and a discharge tip 728. In some implementations, the housing 719 is configured to fluidly seal against the barrel 706, and the aerator 716 may be sealed to the syringe tip 712 and the discharge tip 728, such that any fluid that is ejected from the syringe 703 (e.g., by a user of the syringe 703 depressing the plunger 709) is ejected through the syringe tip 712, into an interior cavity 755 (see FIG. 7B) of the aerator 716, through the discharge tip 728. A circumferential gas pocket 731 may be created by the interior surface 725, the aerator 716, the syringe tip 712, and the discharge tip 728.

Figure 7B:
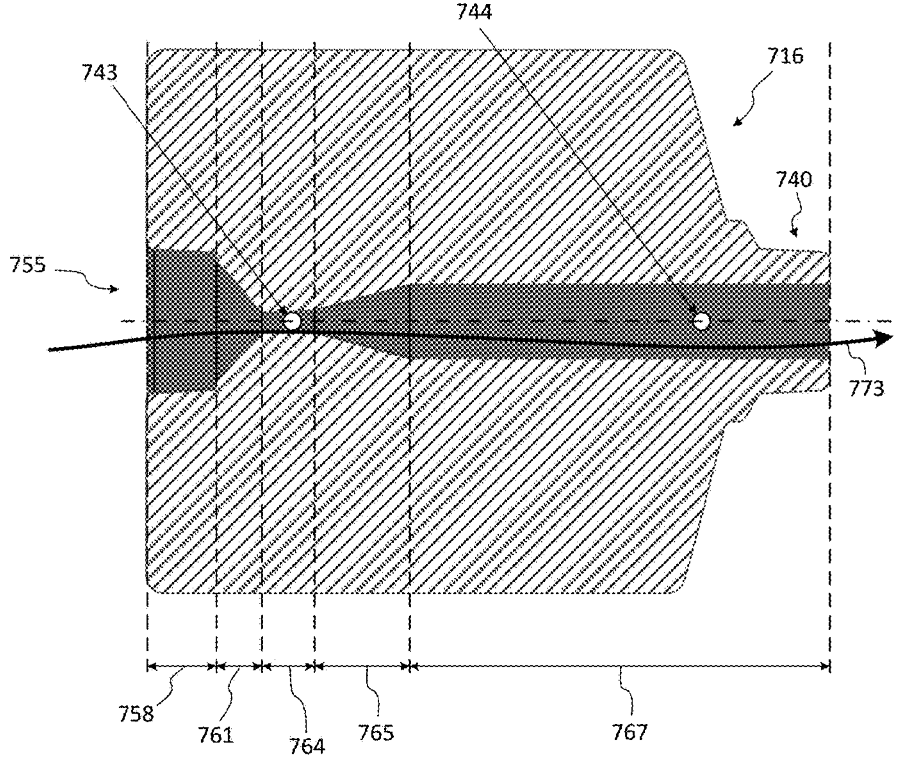
FIG. 7B is a side cross section of an aerator component that may be included in the exemplary microbubble generator of FIG. 7A.

With reference to FIG. 7B, in the implementation shown, the aerator 716 includes an interior cavity 755 that has five discrete sections—an input port section 758, an inlet section 761, a throat section 764, a diffusing section 765, and an outlet section 767. The input port section 758 may be configured to receive the syringe tip 712—that is, the input port section 758 may have a diameter that is only slightly larger than the diameter of the syringe tip 712, and that diameter of the input port section 758 may decrease from outside to inside the input port section 758.

As shown, the inlet section 761 has a progressively decreasing diameter that constricts flow of a gas or liquid through the aerator 716 as that gas or liquid flows from the input port section 758 to a subsequent throat section 764. As described above with respect to other implementations, this constriction of flow of the gas or liquid increases its corresponding velocity and lowers its pressure. This lowering of pressure allows gas to be drawn into the flow through the first vent hole 743.

In some implementations, as shown, a diffusing section 765, having a progressively increasing diameter, follows the throat section 764; and an outlet section 767 follows the diffusing section 765, which outlet section 767 may be cylindrical in structure. In other implementations, the diffusing section 765 and outlet section 767 may be a single section whose diameter progressively increases from the throat section 764 to a tapered outlet port 740.

In some implementations, as shown, a second vent 744 may be disposed in the outlet section 767 (or, in some implementations, the diffusing section 765). In operation, the first vent 743 and second vent 744 may cooperate to increase efficiency at which fluid moving through the throat section 764 aspirates gas, through the first vent hole 743, from the circumferential gas pocket 731 (see FIG. 7A). For example, in some implementations, an initial quantity of fluid passing through the interior cavity 755 may displace air or other gas in the interior cavity 755 primarily through the second vent hole 744, rather than through the first vent hole 743—thereby (i) more quickly pressurizing the circumferential gas pocket 731 and allowing gas in the circumferential gas pocket 731 to be aspirated into the fluid stream moving through the interior cavity 755; and (ii) minimizing the simultaneous movement of a quantity of liquid from the interior cavity 755 into the circumferential gas pocket 731 and movement of gas from the circumferential gas pocket 731 into the interior cavity 755—which simultaneous movement of liquid in one direction and gas in the opposite direction, through the same first vent hole 743, may create turbulence and result in larger bubbles of air being aspirated or formed than would otherwise be the case in implementations that include the second vent hole 744.

In some implementations, the second vent hole 744 is larger than the first vent hole 743. In such implementations, this difference in size, coupled with the difference in pressure of gas, liquid, or a combination thereof in the throat section 764 relative to the outlet section 767, may result in both the liquid itself, and gas that is initially displaced from the interior cavity 755 (e.g., as an initial quantity of fluid flows through said interior cavity 755), flowing from the interior cavity 755 into the circumferential gas pocket 731 primarily through the second vent hole 744.

Regardless of the mechanism of action for any specific implementation, Applicant surprisingly found that a single aerator 716 with both a first vent hole 743 and a second vent hole 744 (e.g., in the outlet section 767, as shown, or in the diffusing section 765) significantly outperformed a single aerator 716 having only a single vent hole 743.

In this context, "performance" may be quantified in terms of (i) production of a significant quantity of very small bubbles (e.g., bubbles having an average diameter of about 300 μm or less; or bubbles having an average diameter of about 250 μm or less; or bubbles having an average diameter of about 200 μm or less; or bubbles having an average diameter of about 100 μm or less; or more preferably, bubbles having an average diameter of less than about 50 μm; or still more preferably, bubbles having an average diameter of less than about 20 μm; or bubbles having an average diameter of less than about 10 μm; or bubbles having an average diameter of less than about 2 μm—note that in some implementations, it may be advantageous to produce bubbles on the higher end of the example ranges provided (e.g., to be more echogenic); whereas in other implementations, it may be advantageous to produce bubbles on the lower end of the example ranges provided (e.g., to more precisely outline internal anatomic features under ultrasound)); and/or (ii) a substantially heterogeneous size distribution of the bubbles produced (e.g., 50% or more of the bubbles falling within one standard deviation of an average bubble size; or 95% of the bubbles falling within one or two standard deviations of an average bubble size; or 99% of the bubbles falling within one, two or three standard deviations of an average bubble size); and/or (iii) with substantially no (or very minimal) production of larger bubbles (e.g., bubbles larger than about 100 μm in diameter, or larger than about 200 μm in diameter, or larger than about 250 μm in diameter, or larger than about 300 μm in diameter).

In some implementations, a boundary between the inlet section 761 and throat section 764 may be rounded and/or smooth (e.g., to minimize turbulence). Similarly, a boundary between the throat section 764 and diffusing section 765 or a boundary between the diffusing section 765 and outlet section 767 may by rounded and/or smooth (e.g., to minimize turbulence). In some implementations, the throat section 764 may have a slight taper (e.g., to facilitate a clean molding process). In some implementations, various surfaces and boundaries may have a rough surface treatment, or edges may be sharp, rather than rounded or smooth (e.g., to increase turbulence).

Figure 8A:
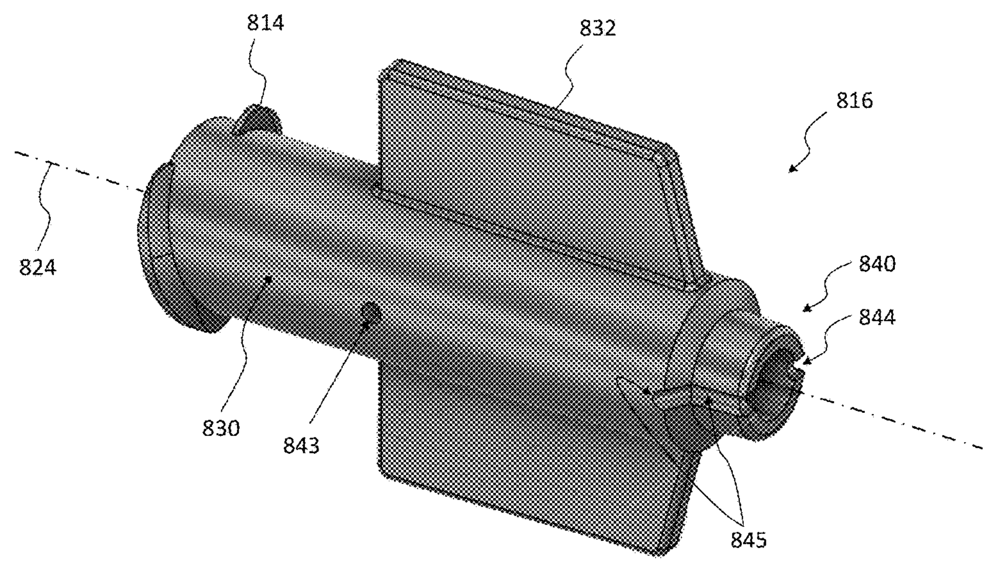
FIG. 8A is a perspective view of an exemplary aerator component.

FIG. 8A is a perspective view of an exemplary aerator component 816. In some implementations, the aerator component 816 may replace the aerator component 716 shown in FIG. 7A. As shown, the aerator component includes threads 814 that may directly interface with mating threads on a corresponding syringe component (e.g., the threads of the Luer lock fitting 713 shown in FIG. 7A). In such implementations, the threads 814 may facilitate a secure, direct connection between the aerator component 816 and a corresponding syringe (e.g., without reliance on a housing component to facilitate that connection).

As shown, the aerator component 816 has an exterior body 830, which, in some implementations, is cylindrical and characterized by a longitudinal axis 824. In other implementations, the exterior body 830 may have other shapes (e.g., rectangular, cubical, triangular, etc.). One or more alignment tabs, such as alignment tab 832, may protrude from the exterior body 830; and such alignment tab(s) 832 may be configured to interface with one or more alignment grooves in a corresponding housing (e.g., alignment grooves 633 in the housing 619, shown in FIG. 6A)—such that when the aerator 816 and corresponding housing are coupled together, the alignment tab(s) 832 and corresponding alignment grooves cooperate to radially fix the housing and aerator component 816 together. When so coupled, the longitudinal axis 824 may align coaxially with longitudinal axes of a corresponding housing and syringe.

Figure 8B:
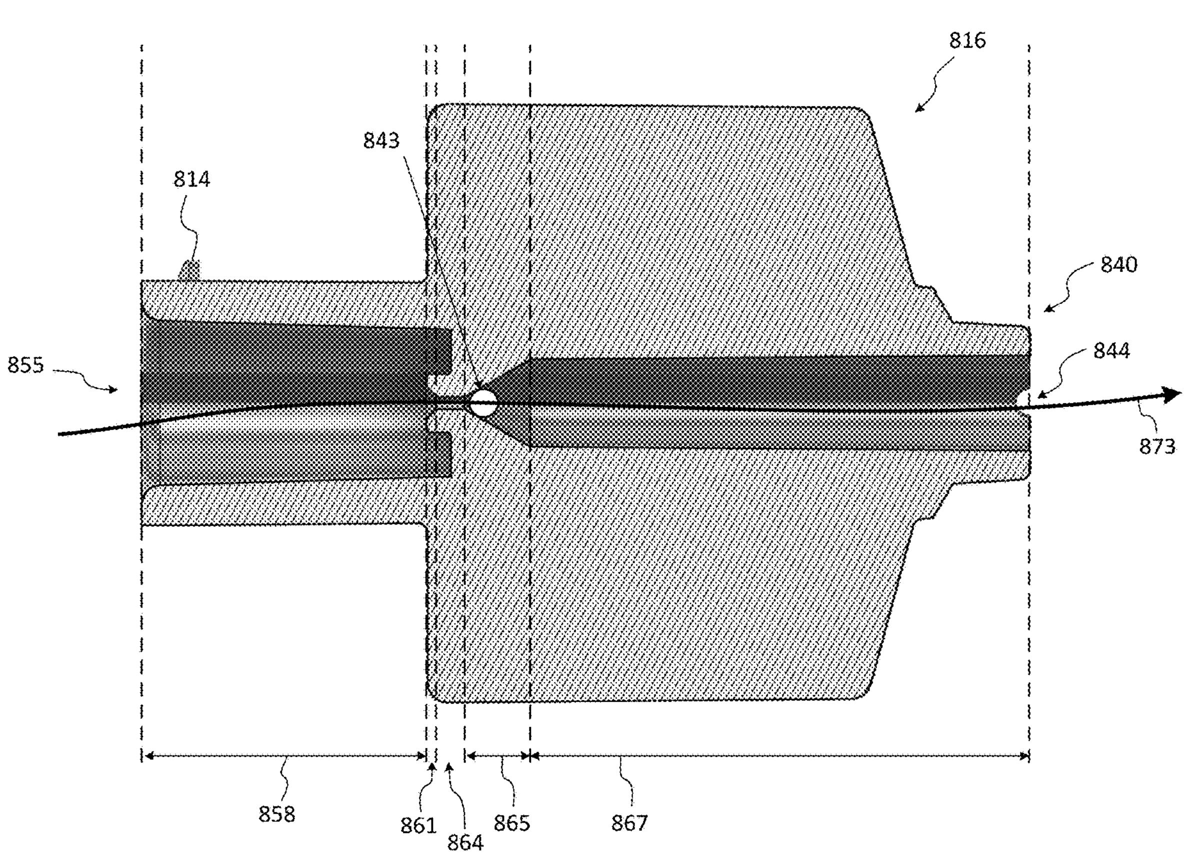
FIG. 8B is a cross section of the aerator component of FIG. 8A.

With reference to FIG. 8B, in the implementation shown, the aerator 816 includes an interior cavity 855 that has five discrete sections, each fluidly coupled to the next to form a flow path 873 through an interior of the aerator 816. The five discrete sections shown include an input port section 858, an inlet section 861, a throat section 864, a diffusing section 865, and an outlet section 867. The input port section 858 may be configured to receive a syringe tip (like the input port 758 of FIG. 7B); and, as noted, threads 814 may be provided to secure the aerator 816 to the syringe tip. The input port section 858 may have a diameter that is only slightly larger than the exterior diameter of the syringe tip, and that diameter of the input port section 858 may decrease from outside to inside the input port section 858 such that the input port section seals against an end of a corresponding syringe tip.

As shown, the inlet section 861 has a progressively decreasing diameter that constricts flow of a gas or liquid through the aerator 816 as that gas or liquid flows from the input port section 858 to a subsequent throat section 864. As described above with respect to other implementations, this constriction of flow of the gas or liquid increases its corresponding velocity and lowers its pressure, which can allow gas to be drawn in through a vent hole 843 in or near the throat section 864.

In the implementation shown, the vent hole 843 is positioned just outside the throat section 864, in a subsequent diffusing section 865, rather than in the throat section 864 itself. As shown, the diffusing section has a progressively increasing diameter and follows the throat section 864; and an outlet section 867 follows the diffusing section 865. In other implementations, the diffusion section 865 and outlet section 867 may be a single section whose diameter progressively increases from the throat section 864 to an outlet port 840.

Although the vent hole 843 is not in the throat section 864 itself, as it is in other implementations illustrated and described herein, the vent hole 843 is disposed close enough to the throat section 864 that the pressure of gas or liquid flowing through the aerator 816, along path 873, is lower at the point of the vent hole 843 than at other portions along the path 873; and this lower pressure allows gas to be drawn into a fluid stream flowing along the path 873, through the vent hole 843.

Figure 8C:
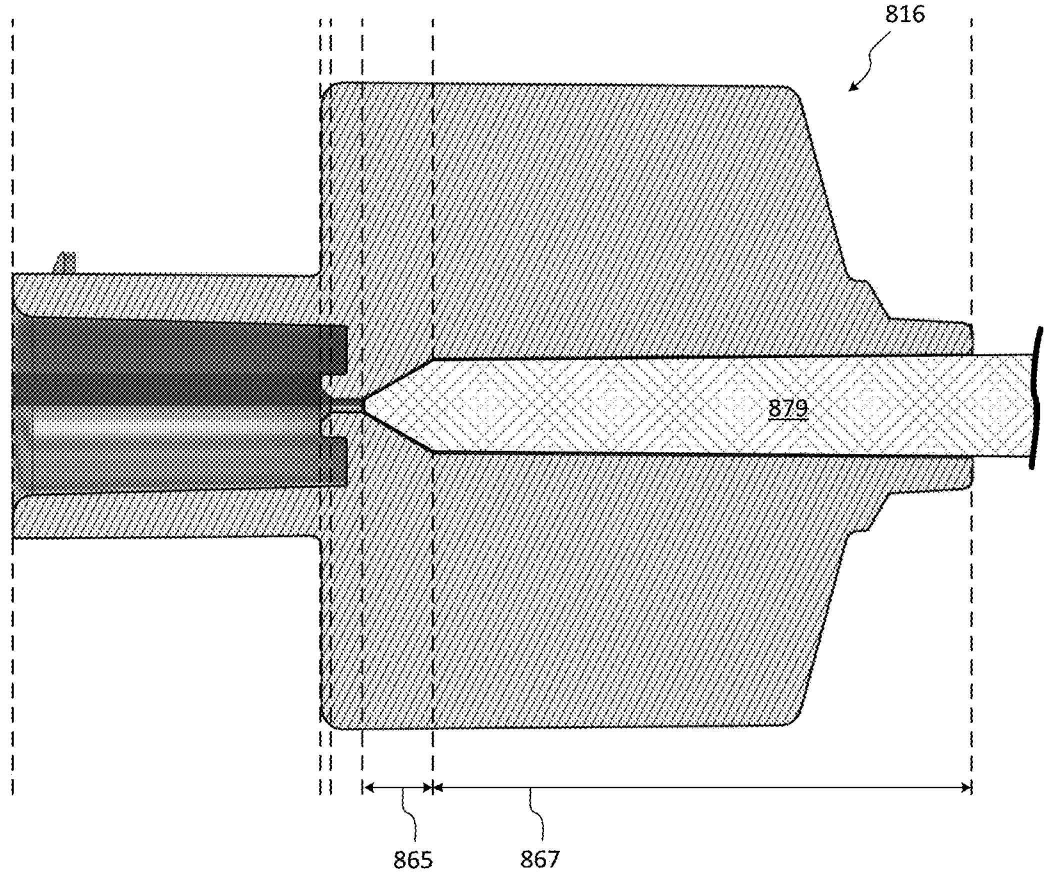
FIG. 8C is a cross section of the aerator component of FIG. 8A, with a sealing pin disposed therein.

Disposition of the vent hole 843 just outside of the throat section 843, in the diffusing section 865—rather than in the throat section 834—can have certain advantages. For example, such an arrangement can facilitate a seal between a sealing pin (such as the sealing pin 679 shown in FIG. 6G) and the vent hole 843, while enabling the sealing pin itself to be larger and more robustly manufactured than would otherwise be possible if such a sealing pin were required to be accommodated by the throat section 864. In some implementations, this may both simplify the manufacturing process and improve the yield on sealing pins; and it may minimize risk of a fragment of a sealing pin breaking off inside the aerator 816 and possibly being introduced into a stream of fluid that is ultimately injected into a patient. FIG. 8C illustrates an exemplary sealing pin 879 and how it may be accommodated by the outlet section 867 and diffusing section 865.

Returning to FIG. 8A, some implementations may include a second vent 844. In the implementation shown, the second vent 844 is disposed at a distal end of the aerator component 816, at an outlet port 840. The second vent 844 may be formed as a notch in a wall of the outlet port 840, and the vent 844 may be fluidly coupled to an area adjacent to the exterior body 830 (e.g., when the aerator component 816 is disposed in a corresponding housing, as in the implementations shown in FIGS. 6A and 7A) via one or more grooves in the exterior body 830, such as the groove 845. In some implementations, implementation of a groove 845 to form the second vent 844 may simplify a manufacturing process, relative to other methods for forming the vent 844. For example, a groove 845 may simplify a mold and molding process, and obviate, in some implementations, the need for a separate pin in the mold to form the vent. In some implementations, a similar approach (e.g., a groove in place of a hole) may be employed for the vent hole 843.

In some implementations, a groove 845 at the outlet port 840 may provide other advantages. For example, when, in a procedure, the device 700 is disposed vertically, with the outlet port 840 directed downward, the groove 845 is positioned at the lowest point of the adjacent gas pocket 731. When fluid in the syringe 703 is nearly expelled, any remaining pressurized air or gas in the gas pocket 731 may expel the last bit of fluid—before the pressure between the gas pocket 731 and the path 873 is equalized—such that no (or very few) bubbles are introduced into the final fluid exiting the outlet port 840. This can be advantageous, because bubbles that are otherwise produced in the last bit of fluid, as that fluid is expelled, may be significantly larger than those created at the vent hole 843. Similar advantages may result from a second vent 744 that is disposed very near the outlet port 740.

Regardless of their precise construction, the vents 843 and 844 may cooperate to increase efficiency at which fluid moving along the path 873 aspirates gas, through the vent hole 843, from a circumferential gas pocket (e.g., like the gas pocket 731 illustrated in FIG. 7A). For example, in some implementations, an initial quantity of fluid passing through the interior cavity 855 may displace air or other gas in the interior cavity 855 primarily through the second vent hole 844, rather than through the vent hole 843—thereby (i) more quickly pressurizing a corresponding circumferential gas pocket and allowing gas in the circumferential gas pocket to be aspirated into the fluid stream moving through the interior cavity 855; and (ii) minimizing the simultaneous movement of a quantity of liquid from the interior cavity 855 into the circumferential gas pocket and movement of gas from the circumferential gas pocket into the interior cavity 855—which simultaneous movement of liquid in one direction and gas in the opposite direction, through the same vent hole 843, may create turbulence and result in larger bubbles of air or other gas being aspirated or formed than would otherwise be the case in implementations that include the second vent hole 844.

In some implementations, the second vent hole 844 is larger than the vent hole 843. In such implementations, this difference in size (coupled with the difference in pressure of gas, liquid, or a combination thereof) in the throat and diffusing sections, 864 and 865, respectively, relative to the outlet section 867, may result in both the liquid itself, and gas that is initially displaced from the interior cavity 855 (e.g., as an initial quantity of fluid flows through said interior cavity 855), flowing from the interior cavity 855 into the circumferential gas pocket primarily through the second vent hole 844.

In some implementations, materials for one or more of the components of the exemplary implementations described herein may be selected based on (a) suitability for use with human patients (i.e., suitable for contact with body-compatible solutions that are to be injected into human patients); (b) solid surface energy (SFE) (e.g., of various components); and (c) interfacial tension (e.g., of the body-compatible solution). The various components described herein may be further selected from materials that are commonly used for the construction of medical devices. Such materials may be selected by virtue of widespread acceptance in the medical device field and/or ability to be sterilized or inherent sterile and/or antimicrobial or antibacterial properties.

With respect to SFE, the material used (e.g., in particular for the aerator or aerator components, such as aerator components 616_a_, 616_b_ and 616_c_ in FIGS. 6A-6G, aerator 716 in FIG. 7A, or aerator 816 in FIG. 8A) may be selected from among thermoplastics or other materials that may be injection molded and that are accepted for use in medical devices—including, for example, polyethylene (in high or low densities), polypropylene, polymethyl methacrylate (PMMA), polyvinyl chloride (PVC), polyamide, acrylonitrile butadiene styrene (ABS), polycarbonate, acetal, polyethylene terephthalate glycol (PETG), or other suitable materials.

More preferentially, in some implementations, the material used may be further selected based on the SFE of the material. For example, in some implementations, it may be advantageous to have a material with an SFE of greater than about 30 millinewtons/meter ("mN/m") (sometimes expressed alternatively as dynes/cm, where 1 mN/m=1 dyne/cm)—in such implementations, a PVC (with an SFE of about 35 mN/m, in some forms), ABS (with an SFE of about 35 mN/m, in some forms), acetal (with an SFE of about 36 mN/m, in some forms), PMMA (with an SFE of about 41 mN/m, in some forms), polycarbonate (with an SFE of about 46 mN/m, in some forms) or PETG (with an SFE of about 47 mN/m, in some forms) may be selected over polypropylene (with an SFE of about 30 mN/m, in some forms) or a polyethylene (with an SFE of about 30 mN/m, in some forms). In other implementations, it may be advantageous to have a material with an SFE of greater than about 35 mN/m. In still other implementations, it may be advantageous to have a material with an SFE of greater than about 40 mN/m—in such implementations, a PMMA, polycarbonate or PETG may be employed.

In some implementations, a material may be treated to raise, lower or otherwise control its SFE (e.g., the surface may be roughened to increase its surface energy, it may be treated chemically, it may be coated with another material, it may be plasma treated or plasma activated, etc.). In many implementations, the practical effect on wettability of the fundamental or treated SFE may matter more than the actual effective value of the SFE—that is, wettability (and specifically, a more wettable, rather than less wettable material) may be more important in certain implementations than the specific SFE value.

In some implementations, the body-compatible solution includes a surfactant that lowers an interfacial tension of the solution; or alternatively, the body-compatible solution is one that has an inherently low interfacial tension relative to other body-compatible solutions. For example, in some implementations, the body-compatible solution is dextrose (e.g., D5W, D10W or D50). As another example, in some implementations, the body-compatible solution includes a surfactant such as polysorbate (e.g., 0.001% polysorbate in a saline solution, 0.005% polysorbate in a saline solution, 0.01% polysorbate in a saline solution, 0.1% polysorbate in a saline solution, 1% polysorbate in a saline solution, 10% polysorbate in a saline solution, etc.). In other implementations, other body-compatible surfactants may be used (e.g., nonionic, anionic, cationic, amphoteric surfactants, generally; specific examples may include, among others, propanediol, polyethylene glycol, lecithin, poloxamer, glycerin, hypertonic saline, hydrophobic hydrocarbon chains with hydrophilic heads, caseins, certain proteins, etc.).

Various implementations were tested with respect to microbubble production capability in a benchtop setup, and images captured of each test. Those images appear as FIGS. 9A-9C, 10A-10C, 11A-11C, 12A-12C and 13A-13C. In each test, a device was employed like one of the devices illustrated in and described with reference to FIG. 6A, 7A or 8A—each device included a syringe body and plunger, a housing, and one or more aerator components within the housing; in addition, a 20-gauge needle was disposed on the end of the housing. For each test, the syringe component was filled with approximately 10 mL of a body-compatible solution, and the device was oriented with the needle disposed in a beaker of tap water. Approximately 3-3.5 mL of room air was enclosed by the housing, in the circumferential air pocket. A black backdrop was placed behind the beaker, and lighting was positioned on the side to illuminate microbubbles formed by the device.

In each test, once the syringe was filled and positioned, the plunger of the syringe was manually depressed using a substantially consistent force/speed to force the body-compatible solution through the aerator component(s) and needle, into the beaker of tap water. Depression of the plunger continued until the body-compatible solution was substantially expelled from the syringe.

Each of FIGS. 9A-9C, 10A-10C, 12A-12C, and 13A-13C includes four panels. In these figures, the left-most panel corresponds to a time approximately 0.5 seconds after the plunger was initially depressed; the left-middle panel corresponds to a time approximately 2.5 seconds after the plunger was initially depressed; the right-middle panel corresponds to a time approximately 6.0 seconds after plunger was initially depressed; and the right-most panel corresponds to a time at which the body-compatible solution was substantially expelled. FIGS. 11A-11C include three panels, because in the corresponding examples, the body-compatible solution was expelled from the syringe more rapidly than in the other examples, such that the total time was less than 6.0 seconds after the plunger was initially depressed. In FIGS. 11A-11C, the left and middle panels remain the same as in FIGS. 9A-9C, 10A-10C, 12A-12C, and 13A-13C—namely, these panels correspond to times of approximately 0.5 and 2.5 seconds after the plunger was initially depressed; the right panel corresponds to a time at which the body-compatible solution was substantially expelled (prior to 6.0 seconds).

Each test ("example") and the results thereof are now described in detail. In the descriptions that follow, subjective descriptions of bubble size are provided (e.g., "microbubbles," "very small" bubbles, "small" bubbles, "medium-sized" bubbles and "large" bubbles); these qualitative descriptions are provided to facilitate qualitative comparison. In some implementations, "large" bubbles may be 1 mm or more in diameter (e.g., 1 mm, 2 mm, 3 mm, 5 mm, etc.); "medium-sized" bubbles may have diameters ranging from about 0.5 mm to about 1 mm; "small" bubbles may have diameters ranging from about 0.1 mm (100 μm) to about 0.5 mm; "very small" bubbles may have diameters ranging from about 10 μm to about 100 μm; and "microbubbles" may have diameters ranging from about 1 μm to about 10 μm. In other implementations, different ranges may apply—for example, in some implementations, "microbubbles" may have diameters less than 1 μm (and may include what could be referred to as "nanobubbles"); as another example, "microbubbles" may include bubbles having diameters of about 1 μm to about 25 μm; as another example, "very small" bubbles may have diameters ranging from 2 μm to about 50 μm. Many specific ranges are possible; and as stated, the primary point of the bubble size references is for qualitative comparison.

Example 1 (Multi-Stage, Polypropylene, Saline)

In a first example, illustrated in FIG. 9A, a device having multiple aerator components (e.g., like the exemplary microbubble generator 600 shown in FIG. 6), each made of polypropylene, was employed; and the syringe was filled with saline. As captured in the left-most panel, initial expulsion of the saline resulted in production of a minimal volume of small to medium-sized bubbles. Bubble production continued to be intermittent and minimal as the saline was expelled from the syringe (note that some small and medium-sized bubbles are visible in solution in the left-middle and right-middle panels). After about 8.5 seconds (see right-most panel), when the saline was substantially expelled, a significant volume of large bubbles was produced.

Example 2 (Multi-stage, Polypropylene, Dextrose)

In a second example, illustrated in FIG. 9B, a device having multiple aerator components, each made of polypropylene, was employed; and the syringe was filled with D50 dextrose (e.g., a solution comprising 50% dextrose). As captured in the left-most panel, initial expulsion of the dextrose resulted in production of a minimal volume of small to medium-sized bubbles. Bubble production was more continuous with the dextrose than with pure saline, and more small bubbles were produced (with medium-sized bubbles also being produced throughout—see left-middle and right-middle panels). A greater quantity of bubbles was produced with dextrose than with saline, but the overall volume remained relatively low. After about 10 seconds (see right-most panel), when the dextrose was substantially expelled, a significant volume of large bubbles was produced.

Example 3 (Multi-Stage, Polypropylene, Saline/Polysorbate)

In a third example, illustrated in FIG. 9C, a device having multiple aerator components, each made of polypropylene, was employed; and the syringe was filled with saline with a small quantity of polysorbate added (approximately 1% by volume). As illustrated in the left-most panel, initial expulsion of the saline/polysorbate resulted in production of a quantity of very small bubbles and microbubbles (as illustrated by the "cloud-like" pattern). After an initial production of very small bubbles, bubble production tapered off with only intermittent production of very small, small and medium-sized bubbles being produced (see left-middle and right-middle panels). After about 9 seconds (see right-most panel), when the saline/polysorbate was substantially expelled, a significant volume of large bubbles was produced.

Example 4 (Multi-Stage, Polycarbonate, Saline)

In a fourth example, illustrated in FIG. 10A, a device having multiple aerator components, each made of polycarbonate, was employed; and the syringe was filled with saline. As illustrated in the left-most panel, initial expulsion of the saline resulted in production of a volume of large bubbles. Steady production of large bubbles continued for approximately two seconds, after which, a steady but minimal stream of small and medium-sized bubbles continued (see left-middle and right-middle panels). After about 11 seconds (see right-most panel), when the saline was substantially expelled, bubble production simply stopped—no large bubbles were produced at the end, as they had been in the previous examples.

Example 5 (Multi-stage, Polycarbonate, Dextrose)

In a fifth example, illustrated in FIG. 10B, a device having multiple aerator components, each made of polycarbonate, was employed; and the syringe was filled with D50 dextrose. As illustrated in the left-most panel, initial expulsion of the dextrose resulted in production of a smooth stream of microbubbles (appearing as a bright cloud). Large bubbles initially accompanied the microbubbles for about two seconds, after which point bubble production slowed slightly (but remained consistent throughout—see left-middle and right-middle panels), and bubble size shifted to mostly very small bubbles. After about 13 seconds (see right-most panel), when the dextrose was substantially expelled, bubble production simply stopped, and no large bubbles were produced at the end.

Example 6 (Multi-Stage, Polycarbonate, Saline/Polysorbate)

In a sixth example, illustrated in FIG. 10C, a device having multiple aerator components, each made of polycarbonate, was employed; and the syringe was filled with saline with a small quantity of polysorbate added (approximately 1% by volume). As illustrated in the left-most panel, initial expulsion of the saline/polysorbate resulted in production of a smooth stream of microbubbles (in a significant quantity, relative to the other examples) with a minimal number of small and very small bubbles (and virtually no medium-sized or large bubbles forming). Steady production of microbubbles continued for about two seconds, after which the volume of bubbles decreased slightly, and the bubbles appeared to increase in size slightly, to very small bubbles (see left-middle and right-middle panels). After about 10.5 seconds (see right-most panel), when the saline/polysorbate was substantially expelled, bubble production tapered off without the production of any large bubbles.

Example 7 (Single-Stage, Polypropylene, Saline)

In a seventh example, illustrated in FIG. 11A, a device having a single aerator component (e.g., like the exemplary microbubble generator 700 shown in FIG. 7) made of polypropylene was employed; and the syringe was filled with saline. As illustrated in the left-most panel, initial expulsion of the saline resulted in production of a quantity of small, medium-sized and large bubbles. Production of these bubbles remained consistent for about one second, after which bubble production diminished, and bubble size decreased (see middle panel). After about 3.5 seconds (see right panel), when the saline was substantially expelled, a significant volume of large bubbles was produced. As evident from the existence of only three panels in FIG. 11A (and FIGS. 11B and 11C), the duration during which bubbles were produced was much shorter in example seven (and examples eight and nine) than in the other examples provided.

Example 8 (Single-Stage, Polypropylene, Dextrose)

In an eighth example, illustrated in FIG. 11B, a device having a single aerator component made of polypropylene was employed; and the syringe was filled with D50 dextrose. As illustrated in the left panel, initial expulsion of the dextrose resulted in production of a quantity of small and medium-sized bubbles. Production of these bubbles remained consistent for about one second, after which bubble production diminished, and bubble size decreased (see middle panel). After about four seconds (see right panel), when the dextrose was substantially expelled, a significant volume of large bubbles was produced.

Example 9 (Single-Stage, Polypropylene, Saline/Polysorbate)

In a ninth example, illustrated in FIG. 11C, a device having a single aerator component made of polypropylene was employed; and the syringe was filled with saline with a small quantity of polysorbate added (approximately 1% by volume). As illustrated in the left panel, initial expulsion of the saline/polysorbate resulted in production of a quantity of microbubbles, with some small and medium-sized bubbles also present. Production of these bubbles remained consistent for about one second, after which bubble production diminished (see middle panel). After about four seconds (see right panel), when the saline/polysorbate was substantially expelled, a significant volume of large bubbles was produced.

Example 10 (Single-Stage, Polycarbonate, Saline)

In a tenth example, illustrated in FIG. 12A, a device having a single aerator component made of polycarbonate was employed; and the syringe was filled with saline. As illustrated in the left-most panel, initial expulsion of the saline resulted in production of a quantity of small, medium-sized and large bubbles. Production of these bubbles remained consistent for about four seconds (see left-middle panel), after which bubble production nearly ceased (see right-middle panel). After about seven seconds (see right-most panel), when the saline was substantially expelled, a significant volume of large bubbles was produced.

Example 11 (Single-Stage, Polycarbonate, Dextrose)

In an eleventh example, illustrated in FIG. 12B, a device having a single aerator component made of polycarbonate was employed; and the syringe was filled with D50 dextrose. As illustrated in the left-most panel, initial expulsion of the dextrose resulted in production of a quantity of small and very small bubbles, with a few medium-sized and large bubbles also present. Production of small and very small bubbles continued for approximately three seconds (see left-middle panel), after which bubble production tapered off somewhat but remained consistent, with small and very small bubbles being produced (see right-middle panel). After about 7.5 seconds (see right-most panel), when the dextrose was substantially expelled, a volume of large bubbles was produced.

Example 12 (Single-Stage, Polycarbonate, Saline/Polysorbate)

In a twelfth example, illustrated in FIG. 12C, a device having a single aerator component made of polycarbonate was employed; and the syringe was filled with saline with a small quantity of polysorbate added (approximately 1% by volume). As illustrated in the left-most panel, initial expulsion of the saline/polysorbate resulted in production of a quantity of small and very small bubbles and microbubbles, with a few medium-sized and large bubbles also present. Production of very small bubbles and microbubbles continued for approximately three seconds (see left-middle panel), after which bubble production tapered off somewhat but remained consistent, with very small bubbles and microbubbles being produced (see right-middle panel). After about 7.0 seconds (see right-most panel), when the saline/polysorbate was substantially expelled, a volume of large bubbles was produced.

Example 13 (Single-Stage, Acetal, Saline)

In a thirteenth example, illustrated in FIG. 13A, a device having a single aerator component made of acetal was employed; and the syringe was filled with saline. As illustrated in the left-most panel, initial expulsion of the saline/polysorbate resulted in production of a quantity of bubbles ranging greatly in size—including large, medium-sized, small and some very small bubbles. Production of bubbles ranging greatly in size continued for approximately three seconds (see left-middle panel), after which bubble production tapered off considerably, with only a small quantity of small and very small bubbles being produced (see right-middle panel). After about 6.5 seconds, medium-sized bubbles were again produced; and at about 8.0 seconds, when the saline was substantially expelled, a volume of large bubbles was produced.

Example 14 (Single-Stage, Acetal, Dextrose)

In a fourteenth example, illustrated in FIG. 13B, a device having a single aerator component made of acetal was employed; and the syringe was filled with D50 dextrose. As illustrated in the left-most panel, initial expulsion of the dextrose resulted in production of a quantity of bubbles ranging greatly in size—including large, medium-sized and small bubbles and some very small bubbles and microbubbles. Production of bubbles ranging greatly in size continued for approximately 3.5 seconds (see left-middle panel), after which bubble production tapered off, with primarily very small bubbles and microbubbles being produced (see right-middle panel). After about 9.0 seconds, when the dextrose was substantially expelled, a volume of large bubbles was produced.

Example 15 (Single-Stage, Acetal, Saline/Polysorbate)

In a fifteenth example, illustrated in FIG. 13C, a device having a single aerator component made of acetal was employed; and the syringe was filled with saline with a small quantity of polysorbate added (approximately 1% by volume). As illustrated in the left-most panel, initial expulsion of the saline/polysorbate resulted in production of small and very small bubbles and microbubbles. Steady production of bubbles in these ranges continued for approximately 4.0 seconds (see left-middle panel), after which bubble quantity tapered slightly but size remained relatively consistent (see right-middle panel). After about 6.5 seconds, when the saline/polysorbate was substantially expelled, a volume of large bubbles was produced.

Analysis of Examples 1-15

As these examples show, Applicant found that, with respect to aerator material and bubble formation, polycarbonate aerators generally outperformed polypropylene aerators—in one or more of length of time over which bubbles were produced (and, by extension, quantity of bubbles) and quality of bubbles (where "higher quality" here corresponds to a distribution that primarily includes small and very small bubbles and microbubbles and that minimizes medium-sized and large bubbles). With single-stage aerators, acetal seemed to perform comparably to polycarbonate. With respect to the solution used in the aerators, dextrose outperformed saline across all examples, though the differences between dextrose and saline were less pronounced with polypropylene aerators. Saline with a small quantity of added polysorbate generally outperformed dextrose across all examples; though, again, differences between saline/polysorbate and dextrose were less pronounced with polypropylene aerators. In contrast to single-staged aerators with either dextrose or polysorbate, multi-staged aerators with either dextrose or polysorbate did not produce large bubbles at the end, when the solution was substantially expelled from the syringe.

Surprisingly, Applicant found that the combination of polycarbonate and dextrose, or polycarbonate and saline/ polysorbate very significantly outperformed (e.g., in bubble quantity and quality, as described above) implementations involving only saline or implementations with polypropylene aerators. Compare, for example, FIG. 10C to the other multi-stage implementations depicted in FIGS. 9A-9C, and FIGS. 10A-10B; further compare FIG. 12C to the other single-stage implementations depicted in FIGS. 11A-11C and FIGS. 12A-12B. Applicant found that acetal and saline/polysorbate performed similar to polycarbonate and saline/polysorbate (see FIG. 13C and FIG. 12C).

Applicant determined that variations in performance in the various examples are related to (1) the surface energy of the material (polypropylene, polycarbonate or acetal in these examples) from which the aerator components are formed—and perhaps more precisely, the corresponding level of hydrophobicity or hydrophilicity that results from said surface energy of the material; and (2) the presence of a surfactant in the body-compatible solution (both dextrose and polysorbate act as surfactants in solution).

Examining these properties independently of each other, various forms of polypropylene have surface energies of about 30 mN/m (milli-Newtons per meter—the International System of Units' standard units for measuring surface energy), whereas various forms of polycarbonate have surface energies of about 46 mN/m. (Various forms of acetal have surface energies of about 36 mN/m—between the surface energies of polypropylene and polycarbonate.) It is believed that the higher surface energy of polycarbonate (and, to a lesser extent, acetal) allows greater spreading of a given solution on the surfaces of the aerator components (e.g., along the channel 773 shown in FIG. 7B or the channel 673 shown in FIG. 6F) than does the lower surface energy of polypropylene—resulting in more efficient operation of the venturi and corresponding vent in introducing air or other gas into the stream of solution flowing past). Put another way, the difference in surface energies is believed to allow less beading of a given solution on polycarbonate (or acetal) than on polypropylene This greater spreading, or less beading, is believed to facilitate greater uptake of air or gas into a stream of solution flowing through the venturi.

Surfactants in solution tend to reduce the interfacial tension between molecules of the solution (independent of effects on interfacial tension that surface energies of materials in contact with the solution may have at the contact surface). That is, in the absence of a surfactant, the intermolecular forces holding individual molecules of the solution to each other may be relatively strong, whereas addition of a surfactant reduces the intermolecular attractive forces, or interfacial tension. It is understood that this reduction of interfacial tension, caused by the presence of a surfactant (e.g., dextrose or polysorbate), increases a solution's ability to attract air or gas, in the form of microbubbles (e.g., in or near the venturi throat, when the solution is moving through said venturi throat).

Surprisingly, Applicant found that variations in these two parameters (surface energy and interfacial tension) combine in a seemingly multiplicative manner rather than merely an additive manner. That is, implementations involving both a higher material surface energy of the aerator components and the presence of a surfactant in the solution facilitated creation of microbubbles that were far superior to bubbles formed in an implementation in which only surface energy was optimized, or only interfacial tension was optimized. For example, with respect to surface energy only, a greater quantity of bubbles were produced by multi-stage aerators having higher surface energies (e.g., more bubbles were produced in example 4 (FIG. 10A) than in example 1 (FIG. 9A)); similarly, a greater quantity of bubbles were produced by single-stage having higher surface energies (e.g., more bubbles were produced in examples 10 and 13 (FIGS. 12A and 13A) than in example 7 (FIG. 11A)). With respect to surfactant only, examples involving dextrose or polysorbate outperformed those involving only saline. However, when these parameters were combined, the differences were very significant—with a multi-stage aerator, bubbles were produced in example 6 (FIG. 10C) in much greater quantity and at much higher quality than those produced in example 3 (FIG. 9C); and with a single-stage aerator, bubbles were produced in examples 12 and 15 (FIG. 12C and FIG. 13C) in much greater quantity and at much higher quality than those produced in example 9 (FIG. 11C). Thus, Applicant surprisingly found that aerator components made of a high surface energy material (e.g., polycarbonate or acetal), combined with a body-compatible solution having a surfactant (e.g., dextrose or polysorbate), produced greater quantities of higher-quality bubbles than other implementations.

Additional Examples

One implementation was further tested to assess ultrasound echogenicity of microbubbles produced and introduced into a live porcine model. Specifically, a multi-stage aerator implementation was employed to produce microbubbles in saline or in a saline/polysorbate solution; the saline or saline/polysorbate solution with microbubbles was injected into the venous system of a live porcine model; and ultrasound images were captured using a transesophageal echocardiogram (TEE). These images appear as FIGS. 14A-14E. Each of these figures comprises a left panel and a right panel. The left panel illustrates the TEE image prior to injection of the solution with microbubbles; and the right panel illustrates the TEE image following injection of the solution with microbubbles.

Example 16 (Current Standard of Care)

FIG. 14A illustrates a TEE taken of a procedure in which microbubbles produced using a current standard-of-care procedure were injected into the venous system of the porcine model. Specifically, two 10 mL syringes were coupled together and to an intravenous line using a three-way stop cock. The intravenous line was disposed in the venous system of the porcine model such that any fluid injected therethrough would be carried to the right atrium of the porcine model. Initially, the stop cock was adjusted to isolate the intravenous line and to couple the two syringes. The first syringe initially contained 9 mL of saline, and the second syringe initially contained 1 mL of room air. The syringe plungers were actuated back and forth 30 times to mix the saline and air and form microbubbles, with all of the saline and air (in the form of microbubbles) ending in one syringe. Then, the stop cock was moved to couple that one syringe to the intravenous line, and the corresponding plunger for that syringe was actuated to inject the saline/microbubble mix into the intravenous line.

Figure 14E:
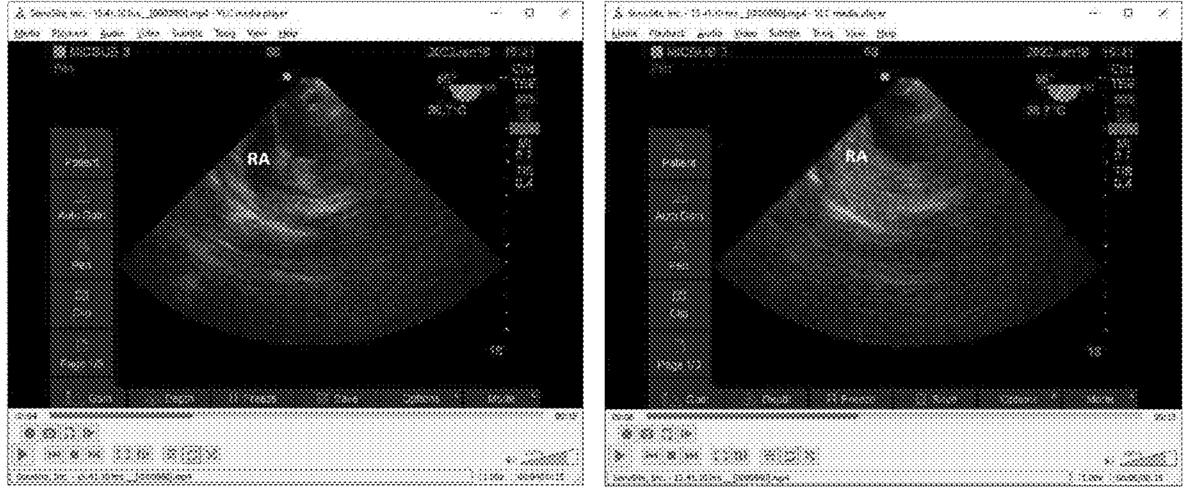
FIG. 14E illustrates a TEE procedure in a porcine model in which a 20-gauge needle was employed to deliver microbubbles, rather than an intravenous line.

The left panel of FIG. 14A illustrates the TEE just prior to the injection. The right atrium is labeled as "RA" in this left panel and in the subsequent panels of FIGS. 14A-14E. For additional anatomical reference, the left atrium and left ventricle are also labeled ("LA" and "LV," respectively) in the left panel of FIG. 14A. In the left panel of FIG. 14A, the "RA" region initially appears dark—indicating a hypoechogenic or anechogenic response associated with blood flowing through the right atrium; in contrast, the tissue forming the wall of the right atrium (and the other tissue structures of the heart) appears lighter in color—indicating a hyperechogenic response that is generally associated with tissue.

The right panel of FIG. 14 illustrates the TEE following the injection. In this panel, the right atrium appears lighter in color—resulting from the hyperechogenic microbubbles appearing in the right atrium following the injection.

Example 17 (Multi-Stage Aerator; Saline with 0.1% Polysorbate)

FIG. 14B illustrates a TEE taken of a procedure in which microbubbles produced using a multi-stage aerator implementation, such as the one illustrated in and described with reference to FIG. 6A. In this example, the input end of a multi-stage aerator was coupled to a 10 mL syringe filled with saline and a 0.1% polysorbate mixture; and the output end of the multi-stage aerator was coupled to the intravenous line disposed in the venous system of the porcine model (again, such that any fluid injected therethrough would be carried to the right atrium of the porcine model).

As in FIG. 14A, the left panel of FIG. 14B illustrates the TEE prior to the injection of the saline/polysorbate/microbubble mixture, and the right atrium is again labeled. After this reference image was captured, the contents of the syringe were injected through the multi-stage aerator and into the intravenous line with a single, steady actuation of the syringe plunger. In contrast to a current standard-of-care procedure captured in and described with reference to FIG. 14A, no agitation of air and saline between multiple syringes was required. By employing the multi-stage aerator, much user-variability associated with creating microbubbles using the current standard-of-care procedure was eliminated.

As shown in the right panel of FIG. 14B, the right atrium again appears lighter in color resulting from hyperechogenic microbubbles appearing in the right atrium following the injection. A comparison of the right panels of FIG. 14A and FIG. 14B reveals a nearly identical ultrasound image. That is, a multi-stage aerator as described herein produces microbubbles of the same quality as those produced using a current standard-of-care procedure, but without user-dependent preparation of air and saline using multiple syringes and a three-way stop cock.

Example 18 (Multi-Stage Aerator; Saline with 0.01% Polysorbate)

FIG. 14C illustrates a TEE taken of a procedure in which microbubbles produced using a multi-stage aerator implementation, such as the one illustrated in and described with reference to FIG. 6A. In this example, the input end of a multi-stage aerator was coupled to a 10 mL syringe filled with saline and a 0.01% polysorbate mixture; and the output end of the multi-stage aerator was coupled to the intravenous line disposed in the venous system of the porcine model (again, such that any fluid injected therethrough would be carried to the right atrium of the porcine model).

Again, the left panel of FIG. 14C illustrates the TEE prior to the injection of the saline/polysorbate/microbubble mixture. After this reference image was captured, the contents of the syringe were injected through the multi-stage aerator and into the intravenous line with a single, steady actuation of the syringe plunger. As shown in the right panel of FIG. 14C, after the injection, the right atrium again appears lighter in color—resulting from hyperechogenic microbubbles appearing in the right atrium following the injection. The ultrasound image quality is comparable to that in Examples 16-17—again equaling that of a current standard-of-care procedure.

Example 19 (Multi-Stage Aerator; Saline with 0.005% Polysorbate)

FIG. 14D illustrates a TEE taken of a procedure in which microbubbles produced using a multi-stage aerator implementation, such as the one illustrated in and described with reference to FIG. 6A. In this example, the input end of a multi-stage aerator was coupled to a 10 mL syringe filled with saline and a 0.005% polysorbate mixture; and the output end of the multi-stage aerator was coupled to the intravenous line disposed in the venous system of the porcine model (again, such that any fluid injected therethrough would be carried to the right atrium of the porcine model).

Again, the left panel of FIG. 14D illustrates the TEE prior to the injection of the saline/polysorbate/microbubble mixture. After this reference image was captured, the contents of the syringe were injected through the multi-stage aerator and into the intravenous line with a single, steady actuation of the syringe plunger. As shown in the right panel of FIG. 14D, after the injection, the right atrium again appears lighter in color—resulting from hyperechogenic microbubbles appearing in the right atrium following the injection. The ultrasound image quality is comparable to that in Examples 16-18—again equaling that of a current standard-of-care procedure.

Example 20 (Multi-Stage Aerator; Saline with 0.005% Polysorbate)

FIG. 14E illustrates a TEE taken of a procedure in which microbubbles produced using a multi-stage aerator implementation, such as the one illustrated in and described with reference to FIG. 6A. In this example, the input end of a multi-stage aerator was coupled to a 10 mL syringe filled with saline and a 0.005% polysorbate mixture; and the output end of the multi-stage aerator was coupled to a 20-gauge needle, which was directly disposed (without any intervening intravenous line) in the venous system of the porcine model (again, such that any fluid injected therethrough would be carried to the right atrium of the porcine model).

The left panel of FIG. 14E illustrates the TEE prior to the injection of the saline/polysorbate/microbubble mixture. After this reference image was captured, the contents of the syringe were injected through the multi-stage aerator and 20-gauge needle with a single, steady actuation of the syringe plunger. As shown in the right panel of FIG. 14E, after the injection, the right atrium again appears lighter in color—resulting from hyperechogenic microbubbles appearing in the right atrium following the injection. The ultrasound image quality is comparable to that in Examples 16-19—again equaling that of a current standard-of-care procedure. As illustrated in this example, there was no perceptible difference in ultrasound image quality between saline/polysorbate/microbubbles being injected through an intravenous line or through a 20-gauge needle.

Analysis of Examples 16-20

As Examples 16-20 illustrate, aerators such as those described herein can produce microbubbles with application for echocardiogram studies and other studies of anatomical structures, such as those utilizing ultrasound and a contrast agent. Moreover, aerators can produce microbubbles from solutions of saline and polysorbate in various concentrations for use in studies of living patients.

Variation in polysorbate concentration may produce effects that are not captured in FIGS. 14B-14E. For example, in some implementations, microbubbles may be smaller with concentrations of polysorbate of approximately 0.1%; and microbubbles in such implementations may be useful in imaging very small anatomic structures (e.g., PFOs, ASDs, or pAVMs). In some implementations, the concentration of polysorbate may influence the time required for microbubbles to dissipate within the circulatory system. Some concentrations may require greater clearance time than other concentrations; thus, by adjusting the polysorbate concentration, one may be able to control clearance time. Polysorbate concentration may also influence precise echogenicity of microbubbles. In some implementations, it may be advantageous to produce microbubbles having greater hyperechogenicity (e.g., to clearly outline a structure); whereas in other implementations, it may be advantageous to produce microbubbles that are merely echogenic (e.g., to facilitate better imaging of adjacent structures).

CONCLUSION

While many implementations are described with reference to heart studies, contrast studies may have other useful applications. For example, microbubbles combined with ultrasound or other imaging technology may be clinically useful in documenting proper catheter placement during pericardiocentesis, central venous catheter placement in the right atrium, and during interventional radiology procedures. In the field of gynecology, for example with ultrasound/infertility procedures, microbubbles may be used to assess patency of the fallopian tubes. Other applications could include imaging of abdominal spaces, portions of the gastrointestinal tract, and joints or other interstitial spaces of a human body. Microbubbles may also be employed in veterinary procedures in a similar manner as described herein.

Several implementations have been described with reference to exemplary aspects, but it will be understood by those skilled in the art that various changes may be made and equivalents may be substituted for elements thereof without departing from the contemplated scope. For example, syringes of various sizes may be employed; a converging nozzle may be integral to the syringe; an aerator may be integral to the converging nozzle; converging nozzles and aerators may be an integral assembly; components may be adhesively joined, ultrasonically welded or molded as unitary parts; some implementations may employ O-rings and compression fittings to join components while other implementations may employ different techniques; different size air channels and geometries may be employed within a converging nozzle; syringes may be prefilled or filled on-site, immediately prior to a procedure; microbubbles may be generated in saline, dextrose, plasma, saline/polysorbate, saline with some other surfactant, or some other body-compatible fluid or combination of fluids; microbubbles may be employed in the context of ultrasound or with other imaging technology; microbubbles may be employed for diagnostic or therapeutic purposes; kits may be provided with any number of microbubble generators, coupled together with a manifold or provided with a manifold for coupling prior to a procedure; different membranes, caps or seals may be employed to contain pre-filled fluid within certain portions of a microbubble generator or microbubble generation system; various numbers of air channels may be employed to facilitate generation of a greater or smaller number of microbubbles per unit of fluid; the air channels may have various dimensions, geometries and/or surface treatment to control size of generated microbubbles; in place of "air" throughout, another gas may be employed (e.g., oxygen, nitrogen, carbon dioxide, some mixture thereof, another biologically compatible gas, etc.); a continuous source of saline or other fluid may replace a syringe; a syringe may be automatically or manually operated; microbubbles may include "nanobubbles" or bubbles of various sizes and distributions; aerator components may vary in dimension (e.g., throat diameter, vent diameter); different numbers of aerator components may be deployed (e.g., one, two, three or more); aerator components may be staged in sequence with different sequences of dimensions (e.g., throats ranging from smaller to larger or in some other sequence); a single-aerator implementation may include different numbers of vent holes (e.g., one, two, three or more); vent holes may be transverse holes that are generally perpendicular to a longitudinal axis of a corresponding channel or flow path; vent holes may be angled relative to a longitudinal axis of a corresponding channel or flow path; vent holes may comprise grooves or other paths that fluidly couple an area exterior to an aerator body to a flow path interior to the aerator body.

Many other variations are possible, and modifications may be made to adapt a particular situation or material to the teachings provided herein without departing from the essential scope thereof. Therefore, it is intended that the scope include all aspects falling within the scope of the appended claims.

What is claimed is:

1. A method for generating microbubbles, comprising:

providing a microbubble generator having:

(a) a syringe having a barrel and a syringe tip and being characterized by a longitudinal axis, wherein the barrel is filled with saline and polysorbate;

(b) an aerator having (i) a generally cylindrical exterior body that is also characterized by a longitudinal axis; (ii) an inlet end; (iii) an outlet end; (iv) a tapered outlet port at the outlet end; and (v) an interior cavity comprising (A) an input port section, (B) a converging section, (C) a throat section, (D) a diverging section, (E) an outlet section, (F) a first vent that fluidly couples at least one of the throat section or the diverging section to an area outside and adjacent to the exterior body, and (G) a second vent that fluidly couples the outlet section to the area; and (c) a housing that (x) circumferentially surrounds an end of the barrel and the aerator, (y) is characterized by a longitudinal axis, (z) has an interior surface, (aa) forms a circumferential gas pocket between the interior surface and the exterior body, and (bb) has a housing discharge tip;

wherein the input port section is configured to accommodate the syringe tip, and the housing discharge tip is configured to accommodate the tapered outlet port, such that the syringe tip, the aerator, and the housing can be coupled together in a coaxial manner relative to their respective longitudinal axes;

coupling the housing discharge tip to a venous system of a patient undergoing a procedure; and generating microbubbles by forcing the saline and polysorbate out of the syringe, through the interior cavity, and through the housing discharge tip.

2. The method of claim 1, wherein the aerator comprises a material having a solid surface energy of about 35 mN/m or more.

3. The method of claim 1, wherein the aerator comprises polycarbonate.

4. The method of claim 1, wherein the aerator comprises one of polycarbonate, polymethacrylate, polyvinyl chloride, polyamide, acrylonitrile butadiene styrene, acetal or polyethylene terephthalate glycol.

5. The method of claim 1, wherein the polysorbate is in a concentration of 0.1% or less.

6. The method of claim 1, wherein the polysorbate is in a concentration of 0.01% or less.

7. The method of claim 1, wherein the polysorbate is in a concentration of 0.005% or less.

8. The method of claim 1, wherein coupling the housing discharge tip to the venous system of the patient comprises coupling the housing discharge tip to a needle and disposing the needle in the venous system of the patient.

9. The method of claim 1, wherein coupling the housing discharge tip to the venous system of the patient comprises coupling the housing discharge tip to an intravenous line and disposing the intravenous line in the venous system of the patient.

10. A method for generating microbubbles, comprising:

providing a microbubble generator having:

a syringe having a barrel and a syringe tip and being characterized by a longitudinal axis, wherein the barrel is filled with saline and polysorbate, wherein the polysorbate is in a concentration of 0.1% or less;

an aerator having a generally cylindrical exterior body that is also characterized by a longitudinal axis; an inlet end; an outlet end; a tapered outlet port at the outlet end; and an interior cavity, the interior cavity comprising an input port section, a converging section, a throat section, a diverging section, an outlet section, a first vent that fluidly couples at least one of the throat section or the diverging section to an area outside and adjacent to the exterior body, and a second vent that fluidly couples the outlet section to the area; and a housing that surrounds an end of the barrel and the aerator, is characterized by a longitudinal axis, has an interior surface, forms a gas pocket between the interior surface and the exterior body, and has a housing discharge tip;

wherein the input port section is configured to accommodate the syringe tip, and the housing discharge tip is configured to accommodate the tapered outlet port, such that the syringe tip, the aerator, and the housing can be coupled together in a coaxial manner relative to their respective longitudinal axes;

coupling the housing discharge tip to a venous system of a patient undergoing a procedure; and generating microbubbles by forcing the saline and polysorbate out of the syringe, through the interior cavity, and through the housing discharge tip.

* * * * *